United States Patent [19]
Chan et al.

[11] Patent Number: 5,514,691
[45] Date of Patent: May 7, 1996

[54] N-(4-HALO-ISOXAZOLYL)-SULFONAMIDES AND DERIVATIVES THEREOF THAT MODULATE THE ACTIVITY OF ENDOTHELIN

[75] Inventors: Ming F. Chan; Bore G. Raju; Rosario S. Castillo; Adam Kois; Chengde Wu; Yalamoori Venkatachalapathi; Erik J. Verner, all of San Diego; Vitukudi N. Balaji, Encinitas, all of Calif.

[73] Assignee: Immunopharmaceutics, Inc., San Diego, Calif.

[21] Appl. No.: 142,552

[22] Filed: Oct. 21, 1993

Related U.S. Application Data

[63] Continuation-in-part of Ser. No. 100,565, Jul. 30, 1993, abandoned, and a continuation-in-part of Ser. No. 100,125, Jul. 30, 1993, abandoned, and a continuation-in-part of Ser. No. 65,202, May 20, 1993, abandoned.

[51] Int. Cl.$^6$ .................. A61K 31/435; C07D 261/06; C07D 215/02
[52] U.S. Cl. .................. 514/312; 514/362; 514/363; 514/378; 514/380; 546/153; 546/155; 546/159; 546/162; 546/167; 546/172; 548/241; 548/243; 548/244; 548/245
[58] Field of Search .................. 548/241, 243, 548/244, 245; 546/153, 155, 159, 162, 167, 172; 514/378, 380, 312, 362, 363

[56] References Cited

U.S. PATENT DOCUMENTS

| | | | |
|---|---|---|---|
| 3,300,488 | 1/1967 | Onoue et al. | 260/239.9 |
| 3,660,383 | 5/1972 | Sumimoto et al. | 260/239.9 |
| 4,997,836 | 5/1991 | Sugihara et al. | 514/253 |
| 5,114,918 | 5/1992 | Ishikawa et al. | 514/11 |
| 5,208,243 | 5/1993 | Peglon et al. | 514/309 |
| 5,270,313 | 12/1993 | Burri et al. | 514/329 |
| 5,378,715 | 1/1995 | Stein et al. | 514/329 |
| 5,389,620 | 2/1995 | Ishikawa et al. | 514/80 |
| 5,389,633 | 2/1995 | Miyake et al. | 514/233.2 |
| 5,407,941 | 4/1995 | Carceller et al. | 514/290 |
| 5,420,123 | 5/1995 | Murugesan | 514/220 |
| 5,420,129 | 5/1995 | Breu et al. | 514/252 |
| 5,420,131 | 5/1995 | Carceller et al. | 514/253 |
| 5,420,133 | 5/1995 | Dhanoa et al. | 514/256 |
| 5,420,138 | 5/1995 | Corbier et al. | 514/300 |
| 5,420,275 | 5/1995 | Masuya et al. | 544/236 |

FOREIGN PATENT DOCUMENTS

| | | |
|---|---|---|
| 5461286 | 3/1985 | Australia . |
| 2067288 | 10/1992 | Canada . |
| 2071193 | 12/1992 | Canada . |
| 0404525 | 12/1990 | European Pat. Off. . |
| 0405421 | 1/1991 | European Pat. Off. . |
| 0436189 | 7/1991 | European Pat. Off. . |
| 0457195 | 11/1991 | European Pat. Off. . |
| 0460679 | 12/1991 | European Pat. Off. . |
| 0558258 | 9/1993 | European Pat. Off. . |
| 0569193 | 11/1993 | European Pat. Off. . |
| 0640596 | 3/1995 | European Pat. Off. . |
| 60-188084 | 9/1985 | Japan . |
| 4-134048 | 5/1992 | Japan . |
| 2259450 | 3/1993 | United Kingdom . |
| 9308799 | 5/1993 | WIPO . |

OTHER PUBLICATIONS (CA): 112(19)178747t, 1989.
CA: 98(25)215517h, 1982.
CA: 94(23)192202c, 1980.
CA: 84(11)73173c, 1975.
CA: 83(23)191975t, 1975.
CA: 80(17)95868c, 1974.
CA: 77(17)113370d, 1972.
CA: 77(13)83384s, 1972.
CA: 73(23)120511w, 1967.
CA: 70(19)87635c, 1968.
CA: 70(1)4103d, 1968.
CA: 67(3)11468t, 1966.
CA: 67(5)21903v, 1965.
CA: 116(23)235529g, 1991.
CA: 116(5)4095m, 1991.
CA: 80(25)146111k, 1974.
CA: 66(19)85762k, 1967.
CA: 111(7)57717d, 1988.
CA: 110(15)135176x, 1987.
CA: 109(18)162247, 1988.
CA: 120(9)94890m, 1991.
CA: 119(25)262066x, 1993.
CA: 119(7)65021c, 1993.
CA: 117(25)245036d, 1992.
CA: 117(13)124085k, 1992.
CA: 117(3)19848p, 1992.
CA: 115(23)247397e, 1991.
CA: 114(17)156648a, 1991.
CA: 114(17)156647z, 1991.
CA: 114(11)95016u, 1990.
CA: 114(7)55340p, 1990.
CA: 114(3)17049t, 1990.
CA: 110(14)121203s, 1988.
CA: 108(23)197876t, 1988.
CA: 107(23)215074r, 1987.
CA: 107(13)108750m, 1987.
CA: 107(9)74639q, 1987.
CA: 105(13)107865z, 1986.
CA: 110(21)185301e, 1989.
CA: 107(23)215074r, 1987.

*Primary Examiner*—Joseph K. McKane
*Attorney, Agent, or Firm*—Stephanie L. Seidman; Brown, Martin, Haller & McClain

[57] ABSTRACT

N-(4-halo-isoxazolyl)sulfonamides and methods for modulating or altering the activity of the endothelin family of peptides are provided. In particular, N-(4-halo-3-isoxazolyl)sulfonamides and N-(4-halo-5-isoxazolyl)benzenesulfonamides and methods for inhibiting the binding of an endothelin peptide to an endothelin receptor or increasing the activity of endothelin peptides by contacting the receptor with a sulfonamide are provided. Methods for treating endothelin-mediated disorders by administering effective amounts of one or more of these sulfonamides or prodrugs thereof that inhibit or increase the activity of endothelin are also provided.

94 Claims, No Drawings

OTHER PUBLICATIONS

CA: 107(13)108750m, 1987.
CA: 107(9)74639q, 1987.
CA: 106(1)110t, 1985.
CA: 104(25)218557z, 1986.
CA: 102(21)182241j, 1985.
CA: 108(11)94444w, 1987.
CA: 108(9)68229k, 1987.
CA: 108(9)68228j, 1987.
CA: 107(13)108750m, 1987.
CA: 93(19)179284r, 1980.
CA: 78(1)77r, 1972.
CA: 76(15)85737n, 1971.
CA: 76(13)68021g, 1971.
CA: 75(1)5884z, 1970.
CA: 116(21)213114r, 1992.
CA: 11(9)74672c, 1989.
CA: 110(21)185301e, 1989.
CA: 109(3)16570r, 1988.
CA: 108(7)54535v, 1988.
CA: 107(23)215074r, 1987.
CA: 107(13)108750m, 1987.
CA: 107(9)74639q, 1987.
CA: 106(7)43380y, 1986.
CA: 106(1)110t, 1985.
CA: 105(13)107865z, 1986.
CA: 104(25)218557z, 1986.
CA: 103(19)153413g, 1985.
CA: 102(21)182241j, 1985.
CA: 102(17)147630p, 1985.
CA: 96(6)40928x, 1981.
CA: 82(17)110544f, 1974.
CA: 80(2)6932d, 1973.
CA: 73(23)120511w, 1970.
CA: 70(19)87639g, 1968.
CA: 70(1)4102c, 1968.
CA: 101(16)137107p, 1984.
CA: 87(1)631c, 1977.CA: 76(11)56259c, 1971.
CA: 74(23)125679n, 1970.
CA: 74(17)87945m, 1970.
CA: 74(11)53764m, 1970.
CA: 73(23)117784g, 1969.
CA: 73(19)98851h, 1970.
CA: 72(19)100676e, 1970
CA: 70(15)68350q, 1968.
CA: 70(13)57821t, 1968.
CA: 68(21)94582v, 1967.
CA: 68(9)39615g, 1967.
CA: 67(7)32627j, 1966.
CA: 67(5)21903v, 1966.
CA: 66(15)65458n, 1967.
CA: 74(17)86290g, 1970.
CA: 72(19)100676e, 1970.
CA: 71(26)128748h, 1967.
CA: 70(9)37686z, 1968.
CA: 69(9)3611a, 1967.
CA: 69(3)10427h, 1967.
CA: 69(2)5219n, 1968.
CA: 66(15)65458n, 1967.
CA: 66(1)1504s, 1966.
CA: 120(13)158152g, 1993.
CA: 120(12)144339m, 1993.
CA: 120(12)144337j, 1993.
CA: 120(9)105206w, 1993.

Fujimoto, et al., "Isoxazole derivatives. II. Synthesis and structure of N–acylsufodiazoles and their homologs", *Chemical Abstracts*, vol. 65, No. 2, Jul. 18, 1966, Abstract No. 2241eq.

Stein, et al., "The Discovery of Sulfonamide Endothelin Antagonsits and the Development of the Orally Active $ET_A$–Antagonist 5– (Dimethylamino)–N–(3, 4–dimethyl–5–isoxazolyl)–1–naphthalenesulfonamide," *J. Med. Chem.* 37(3):329–331 (1994).

Doherty, "Endothelin: A new challenge, " *J. Medicinal Chem.*, 35(9): 1493–1508 (1992).

Bolger et al., "Characterization of binding of the Ca++ channel antagonist [$^3$H]nitrendipine, to guinea–pig ileal smooth muscle," *J. of Pharmacology and Experimental Therapeutics*, 225:291–309 (1983).

Williams et al., "Sarafotoxin S6c: An agonist which distinguishes between endothelin receptor subthpes," *Biochem. and Biophys. Research Commun.*, 175(2):556–561 (1991).

Ihara et al., "An endothelin receptor (ET_) antagonist isolated from *Streptomyces misakiensis*,"*Biochem, and Biophys. Research Commun.*, 178(1):132–137 (1991).

Spinella et al., "Design and synthesis of a specific endothelin 1 antagonist: Effects of pulmonary vasoconstriction," *Proc. Natl. Acad. Sci. USA*, 88p:7443–7446 (1991).

Saeki et al. "[Ala$^{1,3,11,16}$]endothelin–1 analogs with $ET_B$ agonistic activity," *Biochem. and Biophys. Research Commun.*, 179(1):286–292 (1991).

Gu et al., The inhibitory effect of [D–Arg$^1$, D–Phe, D–Try$^{7,9}$, Leu$^{11}$]substances P of endothelin–1 binding sites Panek et al., "Endothelin and structurally related analogs distinguish between endothelin receptor subtypes," *Biochem. and Biophys. Research Commun.*, 183(2):566–571 (1992).

Ihara et al., "Biological profiles of highly potent novel endothelin antagonists selective for the $ET_A$ receptor," *Life Sciences*, 50:247–255 (1991).

Hirata et al., "Receptor binding activity and cytosolic free calcium response by synthetic endothelin analogs in culture rat vascular smooth muscle cells," *Biochem. and Biophys. Research Commun.*, 160:228–234 (1989).

Nakajima et al., "Synthesis of endothelin–1 analogues, endothelin–3, and sarafotoxin S6b: Structure–activity relationships," *J. of Cardiovascular Pharm.*, 13(Suppl. 5):S8–S12 (1989).

Yanagisawa et al., "A novel potent vasoconstrictor peptide produced by vascular endothelial cells," *Nature*, 332:411–415 (1989).

Kashiwabara et al., "Putative precursors of endothelin have less vasoconstrictor activity *in vitro* but a potent pressor effect *in vivo*, *FEBS Letters*, 247(1): 73–76 (1989).

von Geldern et al., "A fluorogenic assay for endothelin–converting enzyme," *Peptide Research*, 4(1):32–35 (1991).

Inoue et al., "The human endothelin family: Three structually and pharmacologically distinct isopeptides predicted by three separate genes," *Proc. Natl. Acad. Sci. USA*, 86:2863–2867 (1989).

Saida et al., "A novel peptide, vasoactive intestinal contractor, of a new (endothelin) peptide family," *J. Biol. Chem.*, 264(25):14613–14616 (1989).

Stewart et al., "Increased plasma endothelin–1 in pulmonary hypertension: Marker or mediator of desease?" *Annals of Internal Medicine*, 114(6)464–469 (1991).

Brooks et al., "Effect of nifedipine on cyclosporine A–induced nephrotoxicity, unirary endothelin excretion and renal endothelin receptor number," *Eur. J. of Pharmacology*, 194:115–117 (1991).

Bolger et al., "Vascular reactivity, tissue levels, and binding sites for endothelin: A comparison in the spontaneously hypertensive and Wistar–Kyoto rats," *Can. J. Physiol. Pharm.*, 69:406–413 (1990).

Simonson et al., "Endothelin–1 stimulates contraction of rate glomerular mesangial cells and potentiaties _-Adrenergic– mediated cyclic adenosine monophosophate accumulation," *J. Clin. Invest.*, 85:790–797 (1990).

Takayanagi et al., "Presence of non–selective type of endothelin receptor on vascular endothelium and its likage to vasodilation," *FEBS Letters*, 282(1):103–106 (1991).

Nishikori et al., "Receptor binding affinity and biological activity of C–terminal elongated forms of endothelin–1," *Neurochem. Int.*, 18(4):535–539 (1991).

Castiglione et al., "Alanine scan of endothelin," Peptides: Chemistry and Biology, Proc. Amer. Rept. Symp. (Twelfth), J. A. Smith and J. E. Rivier, Eds., ESCOM, Leiden, 1992, pp. 402–403.

Galantino et al., "D–Aminor acid scan of endothelin," Peptides: Chemistry & Biology, Proc. Amer. Report. Symp. (Twelfth), J. A. Smith and J. E. Rivier, Eds., ESCOM, Leiden, 1992, pp. 404–405.

Filep et al., "Endothelin–1 induces prostacyclin release from bovine aortic endothelial cells." *Biochem. and Biophys. Research Comm.*, 177(1):171–176 (1991).

Spokes et al., "Studies with endothelin–3 and endothelin–1 on rat blood pressure and isolated issues: Evidence for multiple endothelin receptor subtypes," *J. of Cardiovascular Pharmacology*, 13(Suppl. 5):S191–S192 (1989).

Cardell et al., "Two functional endothelin recedptors in guinea–pig pu;monary arteries," *Neurochem. Int.*, 18(4):571–574 (1991).

Borges et al., "Tissue selectivity of endothelin," *Eur. J. of Pharmacology*, 165:223–230 (1989).

Ogawa et al., "Molecular cloning of a non–isopeptide-selective human endothelin receptor," *Biochem. and Biophys. Research Comm.*, 178(1):248–255 (1991).

Schvartz et al., "Bovine cerebellum endothelin receptor: Solubilization and identification," *Endocrinology*, 126(6):3218–3222 (1990).

Saudek et al., "Solution conformation of endothelin–1 by $^1$H NMR< CD, and nolecular modeling," *Int. J. Peptide Protein Res.*, 37:174–179 (1991).

Aumelas et al., "Determination of the structure of [nLE$^7$] –endothelin by $^1$H NMR," *Int. J. Peptide Protein Res.*, 37:315–324 (1991).

Perkins et al., "Proposed solution structure of endothelin," *Int. J. Peptide Protein Res.*, 36:128–133 (1990).

Spinella et al., "A proposed structural model of endothelin," *Peptide Research*, 2(4):286–291 (1989).

Saudek et al., "$^1$H–NMR study of endothelin, sequence–specific assignment of spectrum and a solution structure," *FEBS Letters*, 257(1):145–148 (1989).

Ramachandran et al., "Conformation of polypeptides and proteins," *Adv. Prot. Chem.*, 23:283–437 (1968).

Szelke et al., "Novel transition–state analogue inhibitors of renin," In *Peptides: Structure and Function, Proceedings of the Eighth American peptide symposium*, (Hruby and Rich, eds.); pp. 579–582, Pierce Chemical Co., Rockford, Illinois (1983).

Allen et al., "The Cambridge crystallgraphic data centre: Computer–based search, retrieval, analysis and display of Information," *Acta Crystallogr.*, B35:2331–2339 (1979).

Weiner et al., "A new force field for molecular mechanical simulation of nucleic acids and proteins," *J. Am. Chem. Soc.*, 106(3):765–784 (Eng.) (1984).

Cooper et al., "A novel approach to molecular similarity," *J. Comput.–Aided Mol. Design*, 3:253–259 (1989).

Brint et al., "Upperbound procedures for the identification of similar three–dimensinal chemical structures," *J. Comput.–Aided Design*, 2:311–310 (1988).

Weiner et al., "An all atom force field for simulations of prteins and nucleic acids," *J. Comput. Chem.*, 7(2):230–252 (1986).

Karplus, M., "Molecular Dynamics: applications to Proteins," in *Computer Simulation of Chemical and Bimolecular Systems*, (Bevendge and Jorfensen, Eds.) *Annals of the New York Acad. Science*, 482:255–266 (1986).

Balasubramanian, R., "New type of representatin for mapping chaim folding in protein molecules," *Nature*, 266:856–857 (1977).

Kemp, D. S., "Peptidminetics and the template approach to nucleation of_–sheets and_–helices in peptides," *Tibtech*, 9:249–255 (1990).

Arai et al., "Cloning and expression of a cDNA encoding an endthelin receptor," *Nature*, 348:730–732 (1990).

De Nucci et al., "Pressor effects of circulating endothelin are limited by its removal in the pulmonary circulation and by the release of prostacyclin and endothelium–derived relaxing factor," *Proc. Natl. Acad. Sci.* 85:9797 (1988).

Morel et al., "increased plasma and plumonary lymph levels of endothelin during endotoxin shock," *Eur. J. Pharm.* 167:427–428 (1989).

Hiley et al., "Functional studies on endothelin catch up with molecular biolgy," *Trends Pharmacol. Sci.* 10:47–49 (1989).

Kaltenbronn et al., "Renin inhibitors containing isosteric replacements of the amide bond connecting the $P_3$ and $P_2$ sites, " *J. Med. Chem.*, 33:838–845 (1990).

Kloog et al., "similarities in mode and sites of action of saraftoxins and endothelins," *Trends Pharmacol. Sci.* 10:212–214 (1989). Maggi et al., "Potent contractile effect of endothelin in isolated guinea–pig airways," *Eur. J. Pharmacol.* 160:179–182 (1989).

Martin et al., "Identification and characterization of endothelin binding sites in rat renal papillary and glomerular membranes," *Biochem. Biophys. Res. Commun.* 162:130–137 (1989).

Palmer et al., "Nitric oxide release accounts for the biological activity of endothelium–derived relaxing factor," *Nature* 327:524–526 (1987).

Saito et al., "Application of monoclonal antibodies for endothelin to hypertensive research," *Hypertension* 15:734–738 (1990).

Sakuri et al., "Cloning of a cDNA encoding a non–isopeptide–selective subtype of the endothelin receptor," *Nature* 348:732–735 (1990).

Takayangi et al., "Multiple subtypes of emdothelin receptors in porcine tissues: characterization by ligand binding, affinity labeling and regional distribution," *Reg. Pep.* 32:23–37 (1991).

Tomita et al., "Plasma endothelin levels in patients with acute renal failure," *N.. Engl. J. Med.* 321:1127 (1989).

Anagnostou et al., "Erythropoitin has mitogenic and positive chemotactic effects of endothelial cells," *P.N.A.S.* 87:5987–5982 (1990).

Buemi et al., "Influence of recombinant erythropoietin on the production of endothelin-1 from human umbilical artery," *Nephron* 64(1):165–166 (1993).

Carlini et al., "Intravenous erythropoietin (rHuEPO) administration increases plasma endothelin and blood pressure in hemodialysis patients," *Am. J. Hyper.* 6:103–107 (1993).

Clark et al., "Endothelin is a potent long-lasting vasoconstrictor in men," *Am. J. Physiol.* 257(6 pt 2):H2033–H2035 (1989).

Eschbach et al., "Recombinant human erythropoietin in anemic patients with end stage renal disease; results of a phase III multicenter Clinical trial," *Ann. Intern. Med.* 111:992–1000 (1989).

Heindenreich et al., "Erythropoietin induces contraction of isolated renal small resistance vessels," *Nephrol. Dial. Transplant* 5:739–740 (1990).

Samtleben et al., "Blood pressure change during ombinant human erythropoietin," *Contrib. Nephrol.* 66:114–122 (1988).

Hori et al., "Hemodynamics and volume changes by recombinant human erythropoitin (rHuEPO) in the treatment of anemic hemodialysis patients," *Clin. Nephrol.* 33:293–298 (1990).

Koyama et al., "Plasma endothelin levels in patients with uremia," *Lancet* 1(8645):991–992 (1989).

Nonnast–Daniel et al., "Atrial natriuretic peptide and central hemodynamics during correction of renal anemia by recombinant human erythropoietin treatment in regular dialysis treatment patients," *Nephrol Dial Transplant* 4:478 (1989).

Raine et al., Effect of erythropoietin on blood pressure," *Am. J. Kid. Dis.* 18(suppl.):76–83 (1991).

Schafter et al., "Treatment of renal anemia with recombinant human erythropoietin," *Am. J. Nephrol.* 8:352–362 (1989).

Sundal et al., "Correction of anemia of chronic renal failure with recombinant human erythropoietin:Safety and efficacy of one year's treatment in a European multicenter study of 150 hemodialysis–dependant patients," *Nephrol Dial Transplant* 4:979–987 (1989).

Tkayama et al., "Effects of recombinant human eryghropoietin on blood coagulation, fibrinolysis and endothelium in hemodialysis patients," *Blood Purif. 1:53–54 (1991).*

Yamashita et al., "Recombinant human erythropoietin (rHuEPO) induces high plasma endothelin (ET) levels in hemodialysis patients," *J. Am. Soc. Nephrol.* 1:409 (1990).

Ohashi et al., "Asterric acid, a new endothelin binding inhibitor," *J. Antiobiotics* 45(10):1684–1685 (1992).

CA 70:37686z Halogenation . . . derivatives. Saito et al., p. 339, 1969.

CA 72:100676e 3—Amino—4—iodo—5—methylisoxazoles with sulfonamide activity. Sumimoto et al., p. 374, 1970.

CA 74:87945m Iodination of isoxazole compounds. Sumimoto et al., p. 436, 1971.

N-(4-HALO-ISOXAZOLYL)-SULFONAMIDES AND DERIVATIVES THEREOF THAT MODULATE THE ACTIVITY OF ENDOTHELIN

RELATED APPLICATIONS

This application is a continuation-in-part of the following applications: U.S. application Ser. No. 08/100,565 to Chan et al., filed Jul. 30, 1993, now abandoned entitled "N-(5-ISOXAZOLYL)-SULFONAMIDES AND DERIVATIVES THEREOF THAT MODULATE THE ACTIVITY OF ENDOTHELIN"; U.S. application Ser. No. 08/100,125 to Chan et al., filed Jul. 30, 1993, now abandoned entitled "N-(3-ISOXAZOLYL)-SULFONAMIDES AND DERIVATIVES THEREOF THAT MODULATE THE ACTIVITY OF ENDOTHELIN", and U.S. application Ser. No. 08/065,202, to Chan, filed May 20, 1993, now abandoned entitled "SULFONAMIDES AND DERIVATIVES THEREOF THAT MODULATE THE ACTIVITY OF ENDOTHELIN".

U.S. application Ser. Nos. 08/100,565 and 08/100,125 are continuation-in-part applications of U.S. application Ser. No. 08/065,202.

The subject matter of U.S. application Ser. Nos. 08/100,565, 08/100,125, 08/065,202 are each incorporated herein in its entirety.

FIELD OF THE INVENTION

The present invention relates to the compounds that modulate the activity of the endothelin family of peptides. In particular, the invention relates to the use of sulfonamides and sulfonamide pro-drugs as endothelin agonists and antagonists.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature.* 288: 373–376). Endothelin, which was originally identified in the culture supernatant of porcine aortic endothelial cells (see, Yanagisawa et al. (1988) *Nature* 332: 411–415), is a potent twenty-one amino acid peptide vasoconstrictor. It is the most potent vasopresser known and is produced by numerous cell types, including the cells of the endothelium, trachea, kidney and brain. Endothelin is synthesized as a two hundred and three amine acid precursor preproendothelin that contains a signal sequence which is cleaved by an endogenous protease to produce a thirty-eight (human) or thirty-nine (porcine) amine acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amine acid intermediate, big endothelin, is hydrolyzed at the $Trp^{21}$—$Val^{22}$ bond to generate endothelin-1 and a C-terminal fragment. A similar cleavage occurs in human cells from a thirty-eight amine acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amine acid peptides and the C-terminal portions of the peptides are identical. Endothelin-2 is ($Trp^6$, $Leu^7$) endothelin-1 and endothelin-3 is ($Thr^2$,$Phe^4$,$Thr^5$, $Tyr^6$,$Lys^7$,$Tyr^{14}$) endothelin-1. These peptides are, thus, highly conserved at the C-terminal ends.

Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194: 115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}$=$4 \times 10^{-10}$M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2-6 \times 10^{-10}$M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137). $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lttrs.* 282: 103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states. Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Endothelin agonists and antagonists

Because endothelin is associated with certain disease states and is implicated in numerous physiological effects, compounds that can interfere with or potentiate endothelin-associated activities, such as endothelin-receptor interaction and vasoconstrictor activity, are of interest. A limited number of compounds that exhibit endothelin antagonistic activity have been identified. In particular, a fermentation product of *Streptomyces misakiensis*, designated BE-18257B, has been identified as an $ET_A$ receptor antagonist. BE-18257B is a cyclic pentapeptide, cyclo(D-Glu-L-Ala-allo-D-Ile-L-Leu-D-Trp), which inhibits $^{125}$I-labelled endothelin-1 binding in cardiovascular tissues in a concentration-dependent manner ($IC_{50}$ 1.4 μM in aortic smooth muscle, 0.8 μM in ventricle membranes and 0.5 μM in cultured aortic smooth muscle cells), but fails to inhibit binding to receptors in tissues in which $ET_B$ receptors predominate at concentrations up to 100 μM. Cyclic pentapeptides related to BE-18257B, such as cyclo(D-Asp-Pro-D-Val-Leu-D-Trp)(BQ-123), have been synthesized and shown to exhibit activity as $ET_A$ receptor antagonists (see, Ishikawa et al. U.S. Pat. No. 5,114,918; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors.

The analog [$Ala^{1,3,11,15}$]endothelin-1, in which the four Cys residues are replaced with Ala, inhibits $^{125}$I-endothelin-1 binding to cerebral membranes, in which $ET_B$ receptors predominate (Hiley et al. (1989) *Trends Pharmacol. Sci* 10: 47–49). This peptide and certain truncated forms of endothelin-1 elicit endothelium-dependent vasorelaxation of precontracted porcine pulmonary arteries to an extent that parallels the respective binding affinities of each form for $ET_B$ (Saeki et al. (1991) *Biochem. and Biophys Res. Commun.* 179: 286–292).

Endothelin antagonists and agonists as therapeutic agents

In view of the numerous physiological effects of endothelin and its apparent association with certain diseases, endothelin is believed to play a critical role in pathophysiological conditions, including hypertension, atherosclerosis, other vascular disorders, gastrointestinal disorders, renal failure, asthma, pulmonary hypertension, endotoxin shock, coronary vasospasm, cerebral vasospasm and others (see, e.g., Saito et al. (1990) *Hypertension* 15: 734–738; Tomita et al. (1989) *N.Engl.J. Med.* 321: 1127; Doherty (1992) *J. Med. Chem.* 35: 1493–1508; Morel et al. (1989) *Eur. J. Pharmacol.* 167: 427–428). Because endothelin is associated with these and other disease states, more detailed knowledge of the function and structure of the endothelin peptide family should provide insight in the progression and treatment of such conditions.

To aid in gaining this understanding, there is a need to identify compounds that modulate or alter endothelin activity. Compounds that modulate endothelin activity, particularly compounds that act as specific antagonists or agonists, may not only aid in elucidating the function of endothelin, but may be therapeutically useful. In particular, compounds that specifically interfere with the interaction of endothelin peptides with the $ET_A$, $ET_B$ or other receptors should aid in the design of therapeutic agents, and may be useful as disease specific therapeutic agents.

Therefore, it is an object herein to provide compounds that have the ability to modulate the biological activity of one or more of the endothelin isopeptides. It is another object to provide compounds that have use as specific endothelin antagonists. It is also an object to use compounds that specifically interact with or inhibit the interaction of endothelin peptides with $ET_A$ or $ET_B$ receptors as therapeutic agents for the treatment of endothelin-mediated diseases and disorders.

SUMMARY OF THE INVENTION

Compounds and methods for inhibiting the binding of an endothelin peptide to $ET_A$ or $ET_B$ receptors and compounds and methods for increasing endothelin receptor-mediated activity of an endothelin peptide are provided. The methods are effected by contacting the receptors with one or more sulfonamides prior to, simultaneously with, or subsequent to contacting the receptors with an endothelin peptide. The sulfonamides are substituted or unsubstituted monocyclic or polycyclic aromatic or heteroaromatic sulfonamides, such as benzene sulfonamides and naphthalene sulfonamides.

The sulfonamides have formula I:

(I)

in which $Ar^1$ is a substituted or unsubstituted aryl group with one or more substituents, including an alkyl group, an aryl group, a substituted aryl group, a nitro group, an amino group or a halide. $Ar^1$ is preferably a five or six membered substituted or unsubstituted aromatic or heteroaromatic ring, including, 3- or 5-isoxazolyl, 2-thiazolyl, 2-pyrimidinyl, or substituted benzene groups, including aryloxy substituted benzene groups.

$Ar^1$ is preferably selected from:

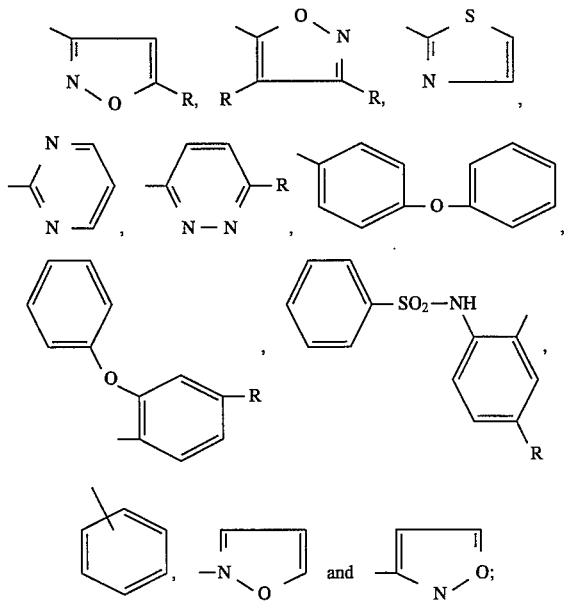

and R is selected from H, $NH_2$, halide, pseudohalide, alkyl alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceding groups, and unsubstituted or substituted with any of the preceding groups, and straight or branched chains of from about 1 up to about 10–12 carbons, preferably, 1 to about 5 or 6 carbons. R is preferably H, $NH_2$, halide, $CH_3$, $CH_3O$ or another aromatic group. $Ar^2$ is alkyl, alkenyl, or is a group selected from:

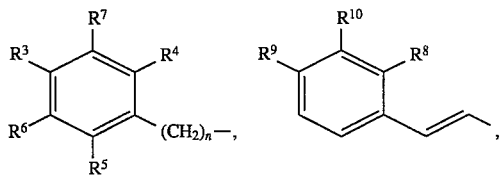

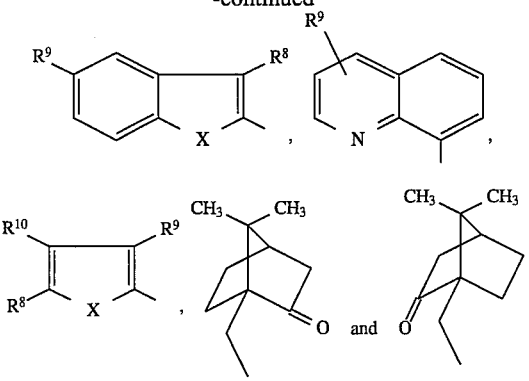

in which $R^3$, $R^4$, $R^5$, $R^6$, $R^7$, $R^8$, $R^9$, $R^{10}$ and $R^{11}$ are each selected independently from among (i), (ii), (iii) or (iv) as follows::

(i) $R^3$, $R^4$, $R^5$, $R^6$, and $R^7$ are each selected independently from among H, NHOH, $NH_2$, $NO_2$, $N_3$, aminoalkyl, alkylamino, dialkylamino, carboxyl, carbonyl, hydroxyl, halide, pseudohalide, alkyl, alkenyl, alkynyl, aryl, heteroaryl, alkoxy, alkylthio, alkyalkoxy, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido, substituted or unsubstituted ureido in which each of the preceding groups may be unsubstituted or substituted with groups such as those set forth for $R^8$, $R^9$, $R^{10}$ and $R^{11}$, the alkyl, alkenyl, alkynyl-portions are straight or branched chains, acyclic or cyclic, of from about 1 up to about 10 carbons, preferably, 1 to about 5 or 6 carbons and the aryl portions contain from 3 up to about 10 carbons, preferably 3 to 6 carbons; $R^8$, $R^9$ and $R^{10}$ are each independently selected from H, $NH_2$, $NO_2$, alkyl and halide; X is O S, NH or $NR^{11}$ in which $R^{11}$ is selected from H, alkyl, alkylcarbonyl or formyl; and n is from 0 up to about 6, and preferably 0 up to about 3 and more preferably 0, 1 or 2; or, alternatively, (ii) $R^4$ and $R^7$ together are substituted or unsubstituted 1, 3-butadienyl, 1-chloro-1,3-butadienyl, 4-dimethylamino-1,3-butadienyl, 1-aza-1,3-butadienyl or 2-aza-1,3-butadienyl groups; and n, X, $R^3$, $R^5$, $R^6$, $R^8$, $R^9$, $R^{10}$ and $R^{11}$ are as defined in (i) above; or alternatively, (iii) $R^7$ and $R^3$ together are substituted or unsubstituted 1, 3-butadienyl, 4-dimethylamino-1,3 butadienyl,1 -chloro-1,3-butadienyl, 1-aza-1,3-butadienyl or 2-aza-1,3-butadienyl groups; and n, X, $R^4$, $R^5$, $R^6$, $R^8$, $R^9$, $R^{10}$ and $R^{11}$ are as defined in (i) above; or alternatively, (iv) $R^3$, $R^5$, and $R^7$ are H; $R^8$, $R^9$, $R^{10}$ and $R^{11}$ are as defined in (i); and $R^4$ and $R^6$ are each independently selected from alkyl, alkoxy, halide, amino alkyl, alkylaminoalkyl or dialkylaminoalkyl, which are unsubstituted or substituted with groups, such as any set forth for $R^8$, $R^9$, $R^{10}$ and $R^{11}$, and in which the alkyl and alkoxy groups contain from 1 to 10, preferably 1 to 6 carbons, and are straight or branched chains.

Thus, in certain embodiments herein, $Ar^2$ is a substituted or unsubstituted group selected from among the following: naphthyl, phenyl, biphenyl, quinolyl, styryl, thiophyl, furanyl, isoquinolyl, pyrrolyl, benzofuranyl, thionaphthalyl, indolyl, alkyl, and alkenyl.

The compounds provided herein have formula II:

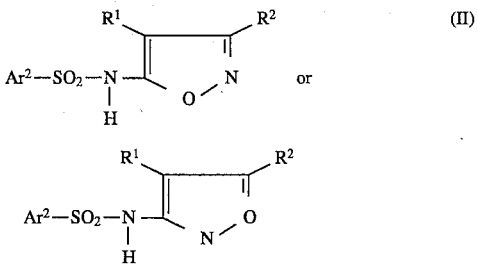

in which $Ar^2$ is defined as above; and $R^1$ and $R^2$ are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons; or, (ii) $R^1$ and $R^2$ together form $—(CH_2)_n—$, where n is 3 to 6; or, (iii) $R^1$ and $R^2$ together form 1,3-butadienyl.

In preferred embodiments, $R^1$ and $R^2$ are selected independently from among alkyl, lower alkenyl, lower alkynyl, lower haloalkyl, halide, pseudohalide or H; $Ar^2$ is as defined above, X is NH, S or O, n is 0 or 1, and $R^3$, $R^4$, $R^5$, $R^6$, $R^7$, $R^8$, $R^9$, $R^{10}$ and $R^{11}$ are selected from (i), (ii), (iii) or (iv) as follows:

(i) $R^4$ and $R^7$ are each independently selected from H, lower alkyl, $NH_2$, $NO_2$, halide, pseudohalide; and $R^3$ is selected from H, NHOH, $NH_2$, $NO_2$, $N_{-3}$, halide, pseudohalide, alkyl, alkenyl, alkynyl, aryl, heteroaryl, alkoxy, alkylamino, alkylthio, alkyalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 5 or 6 carbons and the aryl portions contain from 3 up to about 6 carbons; $R^5$, $R^6$, $R^{10}$ are H; $R^{11}$ is H or $CH_3$; $R^8$ and $R^9$ are each selected independently from among H, $NO_2$, $NH_2$ and halide; or (ii) $R^4$ and $R^7$ together form 1,3-butadienyl, 4-chloro-1,3-butadienyl, 4-dimethylamino-1,3-butadienyl, or 1-aza-1,3-butadienyl; and $R^3$, $R^5$, $R^6$, $R^8$, $R^9$, $R^{10}$ and $R^{11}$ are defined as in (i) of this embodiment or (iii) $R^7$ and $R^3$ together form 1,3-butadienyl, 3-chloro-1,3-butadienyl or 4-dimethylamino-1,3-butadienyl or 1-aza-1,3-butadienyl; and $R^4$, $R^5$, $R^6$, $R^8$, $R^9$, $R^{10}$ and $R^{11}$ are as defined in (i) of this embodiment; or (iv) $R^3$, $R^5$, and $R^7$ are H; $R^8$, $R^9$, $R^{10}$ and $R^{11}$ are as defined in (i); and $R^4$ and $R^6$ are each independently selected from alkyl, alkoxy, halide, amino alkyl, alkylaminoalkyl or dialkylaminoalkyl in which the alkyl and alkoxy groups contain from 1 to 6 carbons, and are straight or branched chains.

In the embodiments provided herein, $Ar^1$ is N-(5-isoxazolyl)or N-(3isoxazolyl) and the compounds have the formula II:

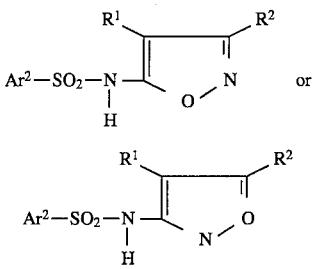

in which $Ar^2$ is as defined above; $R^2$ is selected from among alkyl, lower alkenyl, lower alkynyl, lower haloalkyl, halide or H; and $R^1$ is halide, and in preferred embodiments, $R^1$ is bromide or chloride. Thus, the more preferred compounds herein are N-(4-halo-isoxazolyl)-sulfonamides.

Of the compounds described herein, those that inhibit or increase an endothelin-mediated activity by about 50% at concentrations of less than about 10 μM are preferred. More preferred are those that inhibit or increase an endothelin-mediated activity by about 50% at concentrations of less than about 1 μM, more preferably less than about 0.1 μM, even more preferably less than about 0.01 μM, and most preferably less than about 0.005 μM.

Among the most preferred compounds for use in the methods provided herein, are those that interact with $ET_A$ receptors at concentrations that are too low to detectably interact with $ET_B$ receptors or compounds that interact with $ET_B$ receptors at concentrations that are too low to detectably interact with $ET_A$ receptors. In particular, compounds that interact with $ET_A$ with an $IC_{50}$ of less than about 10 μM, preferably less than 1 μM, more preferably less than 0.1 μM, but with $ET_B$ with an $IC_{50}$ of greater than about about 10 μM or compounds that interact with $ET_B$ with an $IC_{50}$ of less than about 10 μM, preferably less than 1 μM, more preferably less than 0.1 μM, but with $ET_A$ with an $IC_{50}$ of greater than about 10 μM are preferred.

Among others of the preferred compounds for use in the methods herein are any compounds that interact with $ET_A$ and/or $ET_B$ receptors with an $IC_{50}$ of less than about 10 μM, more preferably less than 1 μM, even more preferably less than about 0.1 μM, even more preferably less than about 0.01 μM and most preferably less than about 0.005 μM.

Pharmaceutical compositions formulated for administration by an appropriate route and means containing effective concentrations of one or more of the compounds provided herein or pharmaceutically acceptable salts or acids thereof that deliver amounts effective for the treatment of hypertension, stroke, asthma, shock, ocular hypertension, glaucoma, renal failure, inadequate retinal perfusion and other conditions that are in some manner mediated by an endothelin peptide or that involve vasoconstriction or whose symptoms can be ameliorated by administration of an endothelin antagonist or agonist, are also provided. Particularly preferred compositions are those that deliver amounts effective for the treatment of hypertension or renal failure. The effective amounts and concentrations are effective for ameliorating any of the symptoms of any of the disorders.

Methods for treatment of endothelin-mediated disorders, including but not limited to, hypertension, asthma, shock, ocular hypertension, glaucoma, inadequate retinal perfusion and other conditions that are in some manner mediated by an endothelin peptide, or for treatment of disorder that involve vasoconstriction or that are ameliorated by administration of an endothelin antagonist or agonist are provided.

In particular, methods of treating endothelin-mediated disorders by administering effective amounts of the sulfonamides, prodrugs or other suitable derivatives of the sulfonamides are provided. In particular, methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, endotoxin shock, menstrual disorders, obstetric conditions, wounds, anaphylactic shock, hemorrhagic shock, and other diseases in which endothelin mediated physiological responses are implicated, by administering effective amounts of one or more of the compounds provided herein in pharmaceutically acceptable carriers are provided. Preferred methods of treatment are methods for treatment of hypertension and renal failure.

More preferred methods of treatment are those in which the compositions contain at least one compound that inhibits the interaction of endothelin-1 with $ET_A$ receptors at an $IC_{50}$ of less than about 10 μM, and preferably less than about 5 μM, more preferably less than about 1 μM, even more preferably less than 0.1 μμM, and most preferably less than 0.05 μM. More preferred methods are those in which the compositions contain at least one compound that inhibits the interaction of endothelin-1 with $ET_A$ receptors at an $IC_{50}$ of less than about 100 μM, and preferably less than about 50 μM, more preferably, less than about 10 μM, and even more preferably less than 1 μM, and most preferably less than about 0.1 μM, but do not inhibit binding of endothelin-1 to $ET_B$ receptors at concentrations of about 10 μM or less.

Other preferred methods are those in which the compositions contain at least one compound that inhibits the interaction of endothelin-1 with $ET_B$ receptors at an $IC_{50}$ of less than about 10 μM, and preferably less than about 5 μM, more preferably less than about 1 μM, and even more preferably less than 0.1 μM, and most preferably less than about 0.05 μM. More preferred methods are those in which the compositions contain at least one compound that inhibits the interaction of endothelin-1 with $ET_B$ receptors at an $IC_{50}$ of less than about 100 μM, and preferably less than about 50 μM, more preferably less than about 10 μM, and most preferably less than about 1 μM, but that do not inhibit binding of endothelin-1 to $ET_A$ receptors at concentrations of about 10 μM or less.

In practicing the methods, effective amounts of compositions containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a compound provided herein, which is effective for ameliorating the symptoms of an endothelin-mediated disorder, antagonizing the effects of endothelin or inhibiting binding of an endothelin peptide to an ET receptor with an $IC_{50}$ of less than about 10 μM, within the packaging material, and a label that indicates that the compound or salt thereof is used for antagonizing the effects of endothelin, treating an endothelin-mediated disorder, or inhibiting the binding of an endothelin peptide to an ET receptor are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assess by the ability to interfere with endothelin-induced vasoconstriction.

As used herein, the biological activity or bioactivity of endothelin includes any activity induced, potentiated or influenced by endothelin in vivo. It also includes both the ability to bind to particular receptors and to induce a functional response, such as vasoconstriction. These activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction. Any assay known to those of skill in the art to measure or detect such activity may be used to assess such activity (see, e.g., Spokes et al. (1989) *J. Cardiovasc. Pharmacol.* 13(*Suppl.* 5):S191–S192; Spinella et al. (1991) *Proc. Natl. Acad. Sci. USA* 88: 7443–7446; Cardell et al. (1991) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture, Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392). For example, succinylsulfathiazole is a prodrug of 4-amino-N-(2-thiazoyl)benzenesulfonamide (sulfathiazole) that exhibits altered transport characteristics.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate and azide.

As used herein, lower alkyl, lower alkenyl, and lower alkynyl refer to carbon chains having less than about 6 carbons. In preferred embodiments of the compounds provided herein that include alkyl, alkenyl, or alkynyl portions include lower alkyl, lower alkenyl, and lower alkynyl portions.

As used herein aryl refers to cyclic groups containing from 3 to 15 or 16 carbon atoms, preferably from 5 to 10. The groups may be aromatic or saturated and includes groups, such as phenyl, substituted phenyl, napthyl, substituted naphthyl, in which the substitenent is lower alkyl, halogen, or lower alkoxy.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

A. Compounds for use in treating endothelin-mediated diseases

Compounds and methods for treating endothelin-mediated diseases using the compounds of formula I are provided. The compounds of formula I provided herein are compounds in which $Ar^1$ is N-(5-isoxazolyl) or N-(3-isoxazolyl)that have formula II:

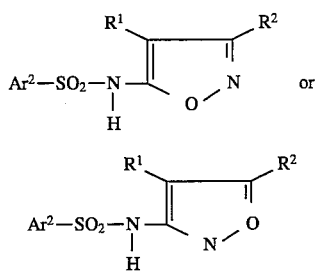

in which $R^2$ is selected from among alkyl, lower alkenyl, lower alkynl, lower haloalkyl, halide, pseudohalide or H; and $R^1$ is halide $Ar^2$ is alkyl or is a group selected from:

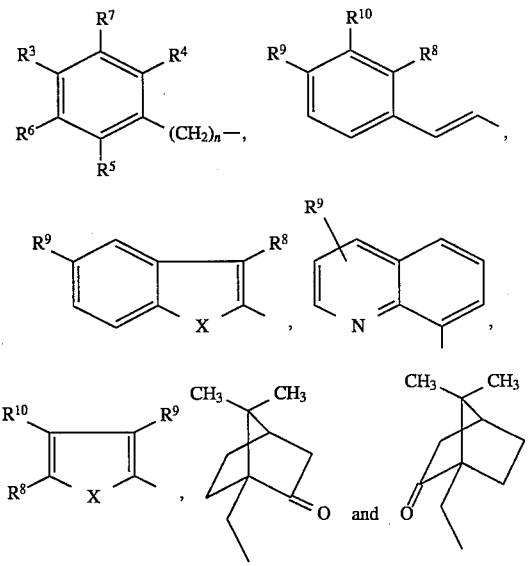

in which:

(i) $R^3$, $R^4$, $R^5$, $R^6$, and $R^7$ are each selected independently from among H, NHOH, $NH_2$, $NO_2$, $N_3$, halide, pseudohalide, alkyl, alkenyl, alkynyl, aryl, heteroaryl, alkoxy, alkylamino, alkylthio, alkyalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynyl portions are straight or branched chains of from about 1 up to about 10 carbons, preferably, 1 to about 5 or 6 carbons and the aryl portions contain from 3 up to about 10 carbons, preferably 6 carbons; $R^8$, $R^9$ and $R^{10}$ are each independently selected from H, $NH_2$, $NO_2$ and halide; X is O, S, NH or $NR^{11}$ in which $R^{11}$ is selected from H, alkyl, alkylcarbonyl or formyl; and n is from 0 up to about 6, and preferably 0 up to about 3 and more preferably 0, 1 or 2; or, alternatively, (ii) $R^4$ and $R^7$ together are substituted or unsubstituted 1,3-butadienyl, 4-dimethylamino- 1,3 butadiene, 1-chloro-1,3-butadiene, 1-aza-1,3-butadienyl or 2-aza-1,3-butadienyl groups; and n, X, $R^3$, $R^5$, $R^6$, $R^8$, $R^9$, $R^{10}$ and $R^{11}$ are as defined in (i) above; or alternatively, (iii) $R^7$ and $R^3$ together are substituted or unsubstituted 1,3-butadienyl, 4-dimethylamino-1,3 butadiene, 1-chloro- 1,3-butadiene, 1-aza-1,3-butadienyl or 2-aza-1,3-butadienyl groups; and n, X, $R^4$, $R^5$, $R^6$, $R^8$, $R^9$, $R^{10}$ and $R^{11}$ are as defined in (i) above, or (iv) $R^3$, $R^5$, and $R^7$ are H; $R^8$, $R^9$, $R^{10}$ and $R^{11}$ are as defined in (i) and $R^4$ and $R^6$ are each independently selected from alkyl, alkoxy, halide aminoalkyl, dialkylaminoalkyl, which are unsubstituted or substituted with alkyl groups, wherein the alkyl and alkoxy groups contain from 1 to 10, preferably 1 to 6 carbons, and are straight or branched chains.

In certain embodiments herein, $Ar^2$ is preferably a substituted or unsubstituted naphthyl group, a substituted or unsubstituted phenyl group, a substituted or unsubstituted biphenyl group, a substituted or unsubstituted quinolyl group, a substituted or unsubstituted styryl group, a substituted or unsubstituted thiophene group, or a substituted or unsubstituted furan group.

In preferred embodiments herein, the compounds have formula II in which $R^1$ is halide, $R^2$, $Ar^2$, $R^3$, $R^5$, $R^6$, $R^8$, $R^9$, $R^{10}$ and $R^{11}$ are as defined above. In most preferred embodiments, $R^1$ is bromide. Thus, the most preferred compounds herein are N-(4-bromo-isoxazolyl)-sulfonamides.

In more preferred embodiments, the compounds are N-(4-halo-isoxazolyl)-sulfonamides in which $Ar^2$ is $CH_3$ or is selected from

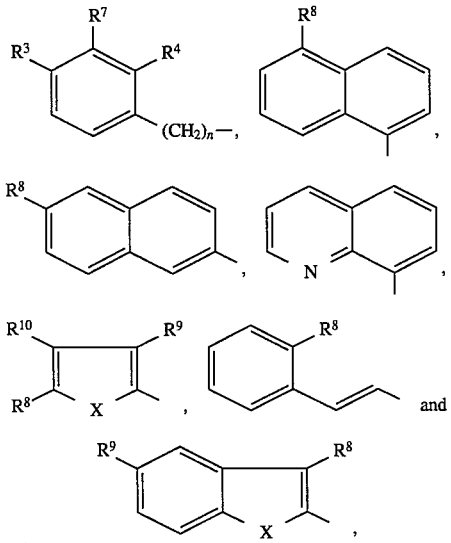

$R^2$ is H, $CH_3$, $C_2H_5$, $H_2C\!=\!CH$, $CH\!\equiv\!C$, Ph—O and 4-$CH_3$—$C_6H_4O$; $R^1$ is Cl or Br; X is O or S; n is 0 or 1; and $R^3$, $R^4$, $R^5$, $R^6$, $R^7$, $R^8$, $R^9$, $R^{10}$ and $R^{11}$ are selected from either (i), (ii), (iii) or (iv) as follows:

(i) $R^8$ is H, $NO_2$, $NH_2$ or halide; $R^5$, $R^6$ and $R^{11}$ are H; $R^4$ and $R^7$ are each independently selected from H, halide, $NH_2$, $CF_3$, Ph, $CH_3$; and $R^3$ is selected from H, NHOH, $NH_2$, $EtNH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n—$C_4H_9O$, $CH_2\!=\!CH$, Ph—CH=CH, CH≡C, Ph—CH≡C, Ph, 3-(ethyoxycarbonylmethyl)ureido, and 3-cyclohexylureido; or (ii) $R^4$ and $R^7$ together form 1,3-butadienyl, 4-chloro-1,3-butadienyl, 4-dimethylamino-1,3-butadienyl or 1-aza-1,3-butadienyl; and $R^3$, $R^5$, $R^6$, $R^8$, $R^9$, $R^{10}$ and $R^{11}$ are defined as in (i) of this embodiment; or (iii) $R^7$ and $R^3$ together form 1,3-butadienyl, 3-chloro-1,3-butadienyl 4-dimethylamino-1,3-butadienyl or 1-aza-1,3-butadienyl; and $R^4$, $R^5$, $R^6$, $R^8$, $R^9$, $R^{10}$ and $R^{11}$ are as defined in (i) of this embodiment; or (iv) $R^3$, $R^5$, and $R^7$ are H; $R^8$, $R^9$, $R^{10}$ and $R^{11}$ are as defined in (i); and $R^4$ and $R^6$ are each independently selected from alkyl, alkoxy, halide, amino alkyl, alkylaminoalkyl or dialkylaminoalkyl, which are unsubstituted or substituted with alkyl groups, in which the alkyl and alkoxy groups contain from 1 to 10, preferably 1 to 6 carbons, and are straight or branched chains.

More preferred among the above compounds are those in which $Ar^2$ is a substituted or unsubstituted phenyl group or naphthyl groups; $R^1$ is Br or Cl; $R^2$ is H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n—$C_3H_7$, iso—$C_3H_7$ and $C_4H_8$; either $R^3$, $R^4$, $R^5$, $R^6$, $R^7$, $R^8$, $R^9$, $R^{10}$ and $R^{11}$ are either (i), (ii), (iii), (iv) or (v):

(i) $R^5$, $R^6$, $R^7$, $R^8$, $R^9$, $R^{10}$ and $R^{11}$ are H; n is 0 and $R^3$ is H, $NH_2$, $CH_3$ $CF_3$, halide, $C_2H_5NH$ or Ph, $R^4$ is H, $CF_3$, $NH_2$, $R^7$ is H or $CF_3$, and $R^5$ and $R^6$ are H; or (ii) $R^3$, $R^5$ $R^6$, $R^8$, $R^9$, $R^{10}$ and $R^{11}$, are H; n is 0 and $R^4$ and $R^7$ together form 1,3-butadienyl, 4-dimethylamino-1,3 butadienyl, 1-chloro-1,3-butadiene, or 4-chloro-1, 3-butadienyl; or (iii) $R^4$, $R^5$, $R^6$, $R^8$, $R^9$, $R^{10}$ and $R^{11}$ are H; n is 0; and $R^7$ and $R^3$ together form 1,3-butadienyl, 4-dimethylamino-1,3 butadienyl, 1-chloro-1,3-butadiene, 1-aza-1,3-butadienyl; or (iv) $R^4$ is H or $NH_2$, $R^5$, $R^6$, $R^7$, $R^8$, $R^9$, $R^{10}$ and $R^{11}$ are H; n is 1 and $R^3$ is H, $NH_2$ and halide; $R^4$ is H, $CH_3$, Br, Cl, F, $CF_3$, $NH_2$, $R^7$ is H, $CH_3$, Br, Cl, F, $CF_3$, and $R^5$ and $R^6$ are H; or (v) $R^3$ $R^5$ and $R^7$ are H; $R^8$, $R^9$, $R^{10}$ and $R^{11}$ are as defined in (i); and $R^4$ and $R^6$ are each independently selected from alkyl groups that contain from 1 to 6 carbons, and are straight or branched chains.

In more preferred embodiments, the compounds are N-(4-halo-isoxazolyl)-sulfonamides in which $R^2$ is H, $CH_3$, $C_2H_5$, $C_2F_5$ or $CF_3$; and $R^3$, $R^4$, $R^5$, $R^6$ and $R^7$ are either (i) or (ii) as follows:

(i) $R^4$, $R^5$, $R^6$ and $R^7$ are each independently selected from H, halide, $NH_2$, $CF_3$, Ph and $CH_3$; $R^3$ is selected from H, NHOH, $NH_2$, $C_2H_5NH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n—$C_4H_9O$, $CH_2=CH$, Ph—CH=CH, $CH\equiv C$, Ph—$CH\equiv C$, Ph, 3-(ethyoxycarbonylmethyl)ureido, and 3-cyclohexylureido and $R^8$, $R^9$, $R^{10}$ and $R^{11}$ are H; or (ii) $R^3$, $R^5$, $R^7$, $R^8$, $R^9$, $R^{10}$ and $R^{11}$ are H; and $R^4$ and $R^6$ are each an alkyl group that contains from 1 to 3 carbons, which are straight or branched chains.

In yet more preferred embodiments, $R^1$ is most preferably Br; $R^2$ is H, $CH_3$, $C_2H_5$, or $CF_3$; $R^8$, $R^9$, $R^{10}$ and $R^{11}$ are H; and $R^3$, $R^4$, $R^6$ and $R^7$ are (i) or (ii) as follows:

(i) $R^3$ is H, $NH_2$, $CH_3$ $CF_3$, halide or $C_2H_5NH$; $R^4$, $R^5$ and $R^6$ are independently selected from H, $CF_3$, halide, particularly Br and Cl, $NH_2$; and $R^7$ is H, $CH_3$, $CH_2CH_5$, $(CH_3)CH$, F or $CF_3$; or (ii) $R^3$, $R^5$ and $R^7$ and $R^4$ and $R^6$ are each an methyl or ethyl.

In all embodiments, $R^1$ is most preferably Br.

Included among the preferred compounds herein are the following:

N-(4-bromo-5-methyl-3-isoxazolyl)benzenesulfonamide;

N-(4-bromo-5-methyl-3-isoxazolyl)-1-naphthalenesulfonamide;

N-(4-bromo-5-methyl-3-isoxazolyl)-4-biphenylsulfonamide;

2-chloro-4-fluoro-N-(5-methyl-3-isoxazoly)benzenesulfonamide;

N-(4-bromo-5-tert-butyl-3-isoxazolyl)benzenesulfonamide;

N-(4-chloro-5-methyl-3-isoxazolyl)benzenesulfonamide;

N-(4-iodo-5-methyl-3-isoxazolyl)benzenesulfonamide;

N-(4-bromo-5-methyl-3-isoxazolyl)-8-quinolinesulfonamide;

4-nitro-N-(4-bromo-5-methyl-3-isoxazolyl)benzenesulfonamide;

5-nitro-N-(4-bromo-5-methyl-3-isoxazolyl)benzenesulfonamide;

5-dimethylamino-N-(4-bromo-3-methyl-5-isoxazoyl)-1-napthalenesulfonamide;

5-dimethylamino-N-(4-bromo-5-methyl-3-isoxazoyl)-1-napthalenesulfonamide;

N-(3-methyl-4-bromo-5-isoxazolyl)benzenesulfonamide;

N-(3-methyl-4-bromo-5-isoxazolyl)-1-naphthalenesulfonamide;

N-(4-bromo-3-phenyl-5-isoxazolyl)benzenesulfonamide;

N-(4-chloro-3-methyl-5-isoxazolyl)benzenesulfonamide;

N-(4-bromo-3-methyl-5-isoxazolyl)-4-biphenylsulfonamide;

N-(4-bromo-3-tert-butyl-5-isoxazolyl)benzenesulfonamide;

4-tert-butyl-N-(4-bromo-3-methyl-5-isoxazolyl)benzenesulfonamide;

N-(4-bromo-3-methyl-5-isoxazolyl)-8-quinolinesulfonamide;

4-iso-propyl-N-(4-bromo-3-methyl-5-isoxazolyl)benzenesulfonamide;

4-bromo-N-(4-bromo-3-methyl-5-isoxazolyl)benzenesulfonamide;

4-fluoro-N-(4-bromo-3-methyl-5-isoxazolyl)benzenesulfonamide;

3-nitro-N-(4 bromo-3-methyl-5-isoxazolyl)benzenesulfonamide;

N-(4-bromo-3-ethyl-5-isoxazolyl)-1-naphthalenesulfonamide;

4-iodo-N-(4-bromo-3-methyl-5-isoxazolyl)benzenesulfonamide;

4-chloro-N-(4-bromo-3-methyl-5-isoxazolyl)benzenesulfonamide;

N-(4-bromo-3-ethyl-5-isoxazolyl)benzenesulfonamide;

N-(4-bromo-3-methyl-5-isoxazolyl)-4-toluenesulfonamide;

2,5-dimethyl-N-(4-bromo-3-methyl-5-isoxazolyl)benzenesulfonamide;

N-(4-bromo-3-methyl-5-isoxazolyl)-2-toluenesulfonamide;

2-fluoro-N-(4-bromo-3-methyl-5-isoxazolyl)benzenesulfonamide;

3-fluoro-N-(4-bromo-3-methyl-5-isoxazolyl)benzenesulfonamide;

2,5-dimethyl-N-(4-chloro-3-methyl-5-isoxazolyl)benzenesulfonamide;

N-(4-chloro-3-methyl-5-isoxazolyl)-4-biphenylsulfonamide;

4-acetamido-N-(4-bromo-3-methyl-5-isoxazolyl)benzenesulfonamide;

4-nitro-N-(4-bromo-3-methyl-5-isoxazolyl)benzenesulfonamide;

4-butoxy-N-(4-bromo-3-methyl-5-isoxazolyl)benzenesulfonamide;

N-(4-bromo-3-methyl-5-isoxazolyl)benzo-2, 1,3-thiadiazole-4-sulfonamide;

N-(4-bromo-3-methyl-5-isoxazolyl)2-thiophenesulfonamide;

3-chloro-2-methyl-N-(4-bromo-3-methyl-5-isoxazolyl)benzenesulfonamide;

2,4,6-trimethyl-N-(4-bromo-3-methyl-5-isoxazolyl)benzenesulfonamide;

N-(4-bromo-3-methyl-5-isoxazolyl)-2-thiophenesulfonamide;

2-methyl-N-(4-bromo-3-methyl-5-isoxazolyl)benzenesulfonamide;

3-chloro- 2,5-dimethyl-N-(4-bromo-3-methyl-5-isoxazolyl)benzenesulfonamide;

2,5-difluoro-N-(4-bromo-3-methyl-5-isoxazolyl)benzenesulfonamide;

2,3-4-trichloro-N-(4-bromo-3-methyl-5-isoxazolyl)benzenesulfonamide;

2,3-dichloro-N-(4-bromo-3-methyl-5-isoxazolyl)benzenesulfonamide;

2,5-dichloro-N-(4-bromo-3-methyl-5-isoxazolyl)benzenesulfonamide;

5-bromo-2-methoxy-N-(4-bromo-3-methyl-5-isoxazolyl)benzenesulfonamide;

2-bromo-N-(4-bromo-3-methyl-5-isoxazolyl)benzenesulfonamide;

2-cyano-N-( 4-bromo-3-methyl- 5-isoxazolyl)benzenesulfonamide;

2,4,5-trichloro-N-(4-bromo-3-methyl-5-isoxazolyl)benzenesulfonamide;

3,4-dichloro-N-(4-bromo-3-methyl-5-isoxazolyl) benzenesulfonamide;

3,4-dimethoxy-N-(4-bromo-3-methyl-5-isoxazolyl)benzenesulfonamide;

2,4-dichloro-N-(4-bromo-3-methyl-5-isoxazolyl)benzenesulfonamide;

4-trifluoromethyl-N-(4-bromo-3-methyl-5-isoxazolyl)benzenesulfonamide;

4-butyl-N-(4-bromo-3-methyl-5-isoxazolyl)benzenesulfonamide;

N-(4-bromo-3-trifluoromethyl-5-isoxazolyl)benzenesulfonamide;

3-chloro-N-(4-bromo-3-methyl-5-isoxazolyl)benzenesulfonamide;

5-chloro-2-methoxy-N-(4-bromo-3-methyl-5-isoxazolyl)benzenesulfonamide;

3-trifluoromethyl-N-(4-bromo-3-methyl-5-isoxazolyl)benzenesulfonamide;

2,5,-diethyl-N-(4-bromo-3-methyl-5-isoxazolyl)benzenesulfonamide; and 2,5-dimethoxy-N-(4-bromo-3-methyl-5-isoxazolyl)benzenesulfonamide.

B. Preparation of the compounds

The compounds, such as N-(4-bromo-3-phenyl-5-isoxazolyl)benzenesulfonamide, for use in the methods herein may be prepared by reacting a sulfonyl chloride with 5-amino-4-bromo-3-methylisoxazole in pyridine solution with 4-(dimethylamino)pyridine as a catalyst. Following the reaction, the pyridine is removed under reduced pressure and the residue is partitioned between water and ethyl acetate. The organic layer is washed and then dried over anhydrous magnesium sulfate, the solvents are evaporated and the residue is purified by column chromatography over silica gel (e.g., 1% methanol in chloroform as eluent)to yielded a solid. Further purification is achieved by recrystallization from ethyl acetate/hexanes, to yield the pure product.

3-Amino-N-(4-bromo-3-methyl-5-isoxazolyl)benzenesulfonamide and 2-amino-N-(4-bromo-3-methyl-5-isoxazolyl)benzenesulfonamide can be prepared by hydrogenation of corresponding nitro-N-(4-bromo-3-methyl-5-isoxazolyl)benzenesulfonamide, which is prepared as described above.

Alternatively, the sulfonamides can be prepared from the corresponding sulfonyl chloride and the aminoisoxazole in tetrahydrofuran solution containing sodium hydride. In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

Exemplary preparations of numerous compounds herein are set forth in the Examples.

Prodrugs and other derivatives of the compounds suitable for administration to humans may also be designed and prepared by methods known to those of skill in the art (see, e.g., Nogrady (1985) *Medicinal Chemistry A Biochemical Approach,* Oxford University Press, New York, pages 388–392.

The above-listed preferred compounds have been synthesized. Nuclear magnetic resonance spectroscopic (NMR), mass spectrometric, infrared spectroscopic and high performance liquid chromatrographic analyses indicated that the synthesized compounds have structures consistent with those expected for such compounds and are at least about 98% pure.

C. Evaluation of the bioactivity of the compounds

Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those of specifically identified herein, that are endothelin antagonists or agonists may be identified using such screening assays.

1. Identifying compounds that modulate the activity of an endothelin peptide

The compounds are tested for the ability to modulate the activity of endothelin-1. Numerous assays are known to those of skill in the art for evaluating the ability of compounds to modulate the activity of endothelin (see, e.g., Ishikawa et al. U.S. Pat. No. 5,114,918; EP A1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., Ishikawa et al. U.S. Pat. No. 5,114,918; EP A1 0 436 189 to BANYU PHARMACEUTICAL CO., LTD. (Oct. 7, 1991))and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., Tissue selectivity of endothelin, *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, Ishikawa et al. U.S. Pat. No. 5,114,918; and EP A1 0 436 189 to BANYU PHARMACEUTICAL CO., LTD (Oct. 7, 1991); see, also Bolger et al. (1983) *J. Pharmacol. Exp. Ther.* 225 291–309). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165:223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al, (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. No. 5,248,807; U.S. Pat. No. 5,240,910; U.S. Pat. No. 5,198,548; U.S. Pat. No. 5,187,195; U.S. Pat. No. 5,082,838; U.S. Pat. No. 5,230,999; published Canadian Application Nos. 2,067,288 and 2071193; published Great Britain Application No. 2,259,450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of endothelin receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptors subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and administration of the compositions

Effective concentrations of one or more of the sulfonamide compounds of formula I or II or pharmaceutically acceptable salts, esters or other derivatives thereof are mixed with a suitable pharmaceutical carrier or vehicle.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations or the compounds are effective for delivery of an amount, upon administration, that ameliorates the symptoms of the endothelin-mediated disease. Typically, the compositions are formulated for single dosage administration.

Upon mixing or addition of the sulfonamide compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semi-liquid or solid form and are formulated in a manner suitable for each route of administration. Preferred modes of administration include oral and parenteral modes of administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., Ishikawa et al. U.S. Pat. No. 5,114,918; EP A1 0 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0.1 mg/ml to about 50–100 µg/ml. The pharmaceutical compositions typically should provide a dosage of from about 0.01 mg to about 2000 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aerosols for topical application, such as by inhalation (see, e.g., U.S. Pat. Nos. 4,044,126, 4,414,209, and 4,364,923, which describe aerosols for delivery of asteroid useful for treatment inflammatory diseases, particularly asthma).

Finally, the compounds may be packaged as articles of manufacture containing packaging material, a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 μM, within the packaging material, and a label that indicates that the compound or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLE 1

N-(4-Bromo-3-methyl-5-isoxazolyl)
benzenesulfonamide (a) 5-Amino-4-bromo-3-methylisoxazole 5-Amino-3-methylisoxazole (0.98 g, 10 mmol) was dissolved in chloroform (15 ml) and cooled to 0° C. N-Bromosuccinimide (1.78 g, 10 mmoles) was added in small portions over a period of 10 min. The stirring was continued for another 10 minutes at 0° C. The reaction mixture was diluted with chloroform (50 ml), washed with water (2×50 ml) and the organic layer was dried over magnesium sulfate. Removal of the solvent under reduced pressure gave the crude product which was purified by column chromatography using 9:1, hexanes/ethyl acetate as eluent to give 5-amino-4-bromo-3-methylisoxazole (1.55 g, 87% yield).

(b) N-(4-Bromo-3-methyl-5-isoxazolyl)
benzenesulfonamide

A solution of 5-amino-4-bromo-3-methylisoxazole (354 mg, 2.0 mmol) in dry THF (1 ml) was added to a suspension of sodium hydride (60% dispersion in mineral oil, 188 mg, 4.4 mmol)in dry THF (1 ml) at 0°–5° C. After stirring at 0°–5° C. for 10 min., the reaction was warmed to room temperature for 10 min. to complete the reaction. The reaction mixture was re-cooled to 0° C. and benzenesulfonyl chloride (0.283 ml, 2.2 mmol) was added slowly. Stirring was continued for 20 min. at 0°–5° C. Excess sodium hydride was decomposed by addition of methanol (0.4 ml) followed by water (0.5 ml). The solvent was removed under reduced pressure. The residue was dissolved in water (20 ml), basified to pH 8–9 by the addition of sodium hydroxide and extracted with ethyl acetate (2×10 ml) to remove the neutral impurities. The aqueous layer was acidified with concentrate HCl (pH 2–3) and extracted with ethyl acetate (3×10 ml) The combined organic layer was dried over magnesium sulfate and concentrated under reduced pressure to give N-(4-bromo-3-methyl-5-isoxazolyl)benzenesulfonamide. The pure material was obtained by recrystallization using hexanes/ethyl acetate (0.59 g, 93% yield), m.p. 142°–144° C.

EXAMPLE 2

N-(4-Bromo-5-tert-butyl-3-isoxazolyl)
benzenesulfonamide (a) 3-Amino-4-bromo-5-tert-butylisoxazole This compound was prepared from 3-amino-5-tert-butylisoxazole and N-bromosuccinimide as described in Example 1a in 91% yield, $R_f$ 0.27 (3:1 hexanes/ethyl acetate).

(b) N-(4-Bromo-5-tert-butyl-3-isoxazolyl)
benzenesulfonamide

3-Amino-4-bromo-5-tert-butylisoxazole (219 mg, 1.0 mmol)was dissolved in dry pyridine (1 ml). Benzenesulfonyl chloride (0.14 ml, 1.1 mmol) and 4-dimethylaminopyridine (5 mg) were added and the solution was stirred at 50 ° C. for 6 h. The reaction mixture was diluted with dichloromethane (75 ml), washed with 1N HCl (50 ml) and dried over anhydrous magnesium sulfate. The solvent was removed under reduced pressure to yield a crude product, which was purified by column chromatography (9:1 hexanes/ethyl acetate). A crystalline solid was obtained after recrystallization from ethyl acetate/hexanes, m.p. 139°–141° C.

EXAMPLE 3

N-(3-Phenyl-4-bromo-5-isoxazolyl)
benzenesulfonamide

This compound was prepared from benzenesulfonyl chloride and 5-amino-4-bromo-3-phenylisoxazole according to the method in Example 1b in 36% yield. Recrystallization from methanol gave a yellow solid, m.p. 113°–115° C.

EXAMPLE 4

N-(4-Bromo-3-tert-butyl-5-isoxazolyl) bensenesulfonamide (IPI-485)

(a) 5-Amino-4-bromo-3-tert-butylisoxazole

5-Amino-4-bromo-3-tert-butylisoxazole was prepared from 5-amino- 3-tert-butylisoxazole and N-bromosuccinimide in 64% yield as described in Example 1a.

(b) N-Benzenesulfonyl-N-(4-Bromo-3-tert-butyl-5-isoxazolyl)benzenesulfonamide 5-Amino-4-bromo-3-tert-butylisoxazole (440 mg, 2.0 mmol) was dissolved in dry pyridine (2 ml). Benzenesulfonyl chloride (344 mg, 2.0 mmol) and 4-dimethylaminopyridine (5 mg) was added and the reaction was stirred at 500° C. for 16 h. The reaction mixture was diluted with ethyl acetate (20 ml), washed with 1N HCl (2×10 ml) and the organic phase was dried over magnesium sulfate. The solvent was removed under reduced pressure to yield a crude product, which was recrystallized from ethyl acetate/hexanes to give 300 mg (60% yield) of N-benzenesulfonyl-N-(4-bromo- 3-tert-butyl-5-isoxazolyl) benzenesulfonamide.

(c) N-(4-Bromo-3-tert-butyl-5-isoxazolyl)benzenelsulfonamide

N-Benzenesulfonyl-N-(4-bromo-3-tert-butyl-5-isoxazolyl)benzenesulfonamide (80 mg, 0. 16 mmol) was dissolved in methanol (2 ml). Sodium hydroxide (0.120 g, 3.0 mmol)in methanol was added and the solution was stirred at 45° C. for 20 min. Methanol was removed under reduced pressure. The residue was dissolved in water, cooled to 0° C. and acidified to pH 3-4 with concentrated hydrochloric acid and extracted with ethyl acetate. The extract was dried over anhydrous magnesium sulfate and concentrated in vacuo to give N-(4-bromo-3-tert-butyl-5-isoxazolyl)benzenesulfonamide in 94% yield. Further purification was achieved by recrystallization from methanol/water, giving an off white solid, m.p. 108°–109° C.

EXAMPLE 5

4-tert-Butyl-N-(4-bromo-3-methyl-5-isoxazolyl)benzenesulfonamide

A solution of 5-amino-4-bromo-3-methylisoxazole (354 mg, 2.0 mmol) in dry THF (1 ml) was added to a suspension of sodium hydride (60% dispersion in mineral oil, 188 mg, 4.4 mmol)in dry THF (1 ml) at 0°–5° C. After stirring at 0°–5° C. for 10 min., the reaction was warmed to room temperature for 10 min. to complete the reaction. The reaction mixture was re-cooled to 0° C. and 4-tert-butylbenzenesulfonyl chloride (512 mg, 2.2 mmol) was added slowly. Stirring was continued for 20 min. at 0°–5° C. Excess sodium hydride was decomposed by addition of methanol (0.4 ml) followed by water (0.5 ml). The mixture was acidified with hydrochloric acid and extracted with dichloromethane. The extract was dried over anhydrous magnesium sulfate and the solvent was removed under reduced pressure to give a crude product, which was purified by recrystallization from ethyl acetate/hexanes to give a white solid in 21% yield, m.p. 170° C. (dec.).

EXAMPLE 6

4-iso-Propyl-N-(4-bromo-3-methyl-5-isoxazolyl)benzenesulfonamide 4-iso-Propyl-N-(4-bromo-3-methyl-5-isoxazolyl)benzenesulfonamide was prepared in the same manner as described in Example 5 from 5-amino-4-bromo-3methylisoxazole and 4-iso-propylbenzenesulfonyl chloride in 77% yield. Purification was achieved by recrystallization from ethyl acetate/hexanes to give a crystalline solid, m.p. 130°–133° C.

EXAMPLE 7

4-Bromo-N-(4-bromo-3-methyl-5-isoxazolyl)benzenesulfonamide

4-Bromo-N-(4-bromo-3-methyl-5-isoxazolyl)benzenesulfonamide was prepared in the same manner as described in Example 5 from 5-amino-4-bromo-3-methylisoxazole and 4-bromobenzenesulfonyl chloride in 74% yield. Purification was achieved by recrystallization from ethyl acetate/hexanes to give a crystalline solid, m.p. 146°–149° C.

EXAMPLE 8

4-Fluoro-N-(4-bromo-3-methyl-5-isoxazolyl)benzenesulfonamide

4-Fluoro-N-(4-bromo-3-methyl-5-isoxazolyl)benzenesulfonamide was prepared in the same manner as described in Example 5 from 5-amino-4-bromo-3-methylisoxazole and 4-fluorobenzenesulfonyl chloride in 71% yield. Purification was achieved by recrystallization from ethyl acetate/hexanes to give a crystalline solid, m.p. 142°–144° C.

EXAMPLE 9

3-Nitro-N-(4-bromo-3-methyl-5-isoxazolyl)benzenesulfonamide

3-Nitro-N-(4-bromo-3-methyl-5-isoxazolyl)benzenesulfonamide was prepared in the same manner as described in Example 5 from 5-amino-4-bromo-3-methylisoxazole and 3-nitrobenzenesulfonyl chloride in 55% yield. Purification was achieved by recrystallization from ethyl acetate/hexanes to give a crystalline solid, m.p. 151°–153° C.

EXAMPLE 10

N-(4-Bromo-5-methyl-3-isoxazolyl) benzenesulfonamide

(a) 3-Amino-4-bromo-5-methylisoxazole

3-Amino-5-methylisoxazole(1.96 g, 20 mmol) was dissolved in chloroform (10 ml) and cooled to 0° C. N-Bromosuccinimide (3.56 g, 20 mmol) was added in small portions over a period of 10 min. The stirring was continued for another 15 minutes at 0° C. The reaction mixture was diluted with chloroform (100 ml), washed with water (2×50 ml) and the organic layer was dried over magnesium sulfate. Removal of the solvent under reduced pressure gave the crude product, which was purified by column chromatography using 9:1, hexanes/ethyl acetate as eluent, to give 3-amino-4-bromo-5-methylisoxazole (1.40 g, 40 % yield).

(b) N-(4-bromo-5-methyl-3-isoxazolyl) benzenesulfonamide and N-(benzenesulfonyl)N-(4-bromo-5-methyl-3-isoxazolyl)benzenesulfonamide 3-Amino-4-bromo-5-methylisoxazole (5.31 g, 30 mmol) was dissolved in dry pyridine (30 ml). Benzenesulfonyl chloride (5.24 ml, 42 mmol) was added dropwise with stirring at ambient temperature. N,N-(Dimethyl)aminopyridine (100 mg) was added and stirring was continued at 50° C. for 25 h. The reaction mixture was diluted with dichloromethane (200 ml), washed with 1N HCl (6×100 ml) and the organic phase was dried over magnesium sulfate. The solvent was removed under reduced pressure to yield a crude product which was purified by column chromatography using 9: 1, hexanes/ethyl acetate as eluent to give N-(benzenesulfonyl)-N-(4-bromo-5-methyl-3-isoxazolyl)benzenesulfonamide (7 g, 51% yield, $R_f$=0.27 using 3:1, hexanes/ethyl acetate as eluent) as a solid.

Further elution with ethyl acetate gave N-(4-bromo-5-methyl-3-isoxazolyl)benzenesulfonamide (2 g, 21% yield, $R_f$=0.08 with 3:1 hexanes/ethyl acetate as eluent), m.p. 128°–130° C.

(c) N-(4-bromo-5-methyl-3-isoxazolyl) benzenesulfonamide

Sodium hydroxide (1.3 g, 30.6 mmol) was added to a solution of N-(benzenesulfonyl)-N-(4-bromo-5-methyl-3-isoxazolyl)benzenesulfonamide (7 g, 15.3 mmol, prepared as described in (a)) in methanol (100 ml). The resulting solution was stirred at 25° C. for 30 h. Excess methanol was removed under reduced pressure. The residue was dissolved in water (50 ml) and acidified (pH 3–4) by the addition of concentrated HCl with cooling. The mixture was extracted with dichloromethane (2×100 ml) and the combined organic layer was dried over anhydrous magnesium sulfate. Removal of the solvent gave N-(4-bromo-5-methyl-3-isoxazolyl)benzenesulfonamide which was purified by crystallization from ethyl acetate/hexanes (4.5 g, 92% yield). The compound is identical to the one isolated in step (b).

EXAMPLE 11

N-(4-Bromo-5-methyl-3-isoxazolyl)-1-naphthalenesulfonamide

N-(4-Bromo-5-methyl-3-isoxazolyl)-1-naphthalenesulfonamide was prepared from 3-amino-4-bromo-5-methylisoxazole and 1-naphthalenesulfonyl chloride as described in Example 2 in 51% yield. Recrystallization from ethyl acetate/hexanes gave a crystalline solid, m.p. 167°–170° C.

EXAMPLE 12

N-(4-Chloro-3-methyl-5-isoxazolyl) benzenesuolfonamide

(a) 5-Amino-4-chloro-3-methylisoxazole

Using the method in Example 1a, 5-amino-4-chloro-3methylisoxazole was prepared in 90% yield from 5-amino-3-methylisoxazole and N-chlorosuccinimide.

(b) N-(4-Chloro-3-methyl-5-isoxazolyl) benzenesuolfonamide

N-(4-Chloro-3-methyl-5-isoxazolyl)benzenesulfonamide was prepared according to the method in Example 1b from 5-amino-4-chloro-3-methylisoxazole and benzenesulfonyl chloride in 84% yield. The crude product was purified by recrystallization using hexanes/ethyl acetate, m.p. 140°–143° C.

EXAMPLE 13

N-(4-Chloro-5-methyl-3-isoxazolyl) benzenesulfonamide

(a) 3-Amino-4-chloro-5-methylisoxazole

This compound was prepared from 3-amino-5-methylisoxazole and N-chlorosuccinimide as described in Example 1a except the reaction was changed to 350° C. and the reaction time was extended to 12 h. The yield was 62%, $R_f$ 0.17 (3:1 hexanes/ethyl acetate).

(b) N-(4-Chloro-5-methyl-3-isoxazolyl) benzenesulfonamide

N-(4-chloro-5-methyl-3-isoxazolyl)benzenesulfonamide was prepared from 3-amino-4-chloro-5-methylisoxazole and benzenesulfonyl chloride as described in Example 2b in 40% yield. The crude product was purified by column chromatography with 10–100% ethyl acetate/hexanes as eluent. A crystalline solid was obtained after recrystallization from ethyl acetate/hexanes, m.p. 139°–141° C. 3-Amino-4-chloro-5-methylisoxazole (25% recovery)and N-(benzenesulfonyl)-N-(4-chloro-5-methyl-3-isoxazolyl-)benzen esulfonamide (7% yield) were also obtained as less polar products.

EXAMPLE 14

4-Iodo-N-(4-bromo-3-methyl-5-isoxazolyl) benzenesulfonamide

4-Iodo-N-(4-bromo-3-methyl-5-isoxazolyl)benzenesulfonamide was prepared from 5-amino-4-bromo-3-methylisoxazole and 4-iodobenzenesulfonyl chloride according to the procedures described in Example 1b. The crude product was purified by recrystallization from ethyl acetate/hexanes to give a yellow powder, m.p. 166°–173° C., yield 65 %.

EXAMPLE 15

4-Chloro-N-(4-bromo-3-methyl-5-isoxazolyl)benzenesulfonamide

4-Chloro-N-(4-bromo-3-methyl-5-isoxazolyl)benzenesulfonamide was prepared from 5-amino-4-bromo-3-methylisoxazole and 4-chloro-benzenesulfonyl chloride according to the procedures described in Example 1b. The crude product was purified by recrystallization from ethyl acetate/hexanes to give a yellow powder, m.p. 145°–150° C., yield 93%.

EXAMPLE 16

N-(4-Bromo-3-ethyl-5-isoxazolyl)benzenesulfonamide (a) 5-Amino-4-bromo-3-ethylisoxazole 5-Amino-4-bromo-3-ethylisoxazole was prepared from 5-amino-3ethylisoxazole and N-bromosuccinimide as described in Example 1a.

(b) N-(4-Bromo-3-ethyl-5-isoxazolyl)benzenesulfonamide

N-(4-Bromo-3-ethyl-5-isoxazolyl)benzenesulfonamide was prepared from 5-amino-4-bromo-3-ethylisoxazole and benzenesulfonyl chloride according to the procedures described in Example 1. The crude product was purified by recrystallization from ethyl acetate/hexanes to give off-white crystals, m.p. 90°–93° C., yield 70%.

EXAMPLE 17

N-(4-Bromo-3-methyl-5-isoxazolyl)-4-toluenesulfonamide

N-(4-Bromo-3-methyl-5-isoxazolyl)-4-toluenesulfonamide was prepared from 5-amino-4-bromo-3-methylisoxazole and 4-toluenesulfonyl chloride according to the procedures described in Example 1b. The crude product was purified by recrystallization from ethyl acetate/hexanes to give off-white crystals, m.p. 169°–172° C., yield 69%.

EXAMPLE 18

2, 5-Dimethyl-N-(4-bromo-3-methyl-5-isoxazolyl)benzenesulfonamide 2, 5-Dimethyl-N-(4-bromo-3-methyl-5-isoxazolyl)benzenesulfonamide was prepared from 5-amino-4-bromo-3-methylisoxazole and 2,5-dimethylbenzenesulfonyl chloride according to the procedures described in Example 1b. The crude product was purified by recrystallization from ethyl acetate/hexanes to give off-white crystals, m.p. 102°–104° C., yield 81%.

EXAMPLE 19

N-(4-Bromo-3-methyl-5-isoxazolyl)-2-toluenesulfonamide

N-(4-Bromo-3-methyl-5-isoxazolyl)-2-toluenesulfonamide was prepared from 5-amino-4-bromo-3-methylisoxazole and 2-toluenesulfonyl chloride according to the procedures described in Example 1b. The crude product was purified by recrystallization from ethyl acetate/hexanes to give white crystalline solid, m.p. 93°–96° C., yield 88%.

EXAMPLE 20

2-Fluoro-N-(4-bromo-3-methyl-5-isoxazolyl)benzenesulfonamide

2-Fluoro-N-(4-bromo- 3-methyl- 5-isoxazolyl)benzenesulfonamide was prepared from 5-amino-4-bromo-3-methylisoxazole and 2-fluorobenzenesulfonyl chloride according to the procedures described in Example 1b. The crude product was purified by recrystallization from ethyl acetate/hexanes to give a white solid, m.p. 87°–89° C., yield 44%.

EXAMPLE 21

3-Fluoro-N-(4-bromo-3-methyl-5-isoxazolyl)benzenesulfonamide

3-Fluoro-N-(4-bromo-3-methyl-5-isoxazolyl) benzenesulfonamide was prepared from 5-amino-4-bromo-3-methylisoxazole and 3-fluorobenzenesulfonyl chloride according to the procedures described in Example 1b. The crude product was purified by recrystallization from ethyl acetate/hexanes to give a light yellow solid, m.p. 125°–128° C., yield 88%.

EXAMPLE 22

2,5-Dimethyl-N-(4-chloro-3-methyl-5-isoxazolyl)benzenesulfonamide 2,5-Dimethyl-N-(4-chloro-3-methyl-5-isoxazolyl)benzenesulfonamide was prepared from 5-amino-4-chloro-3-methylisoxazole and 2,5-dimethylbenzenesulfonyl chloride according to the procedures described in Example 1b. The crude product was purified by recrystallization from ethyl acetate/hexanes to give a light yellow solid, m.p. 92°–93° C., yield 82%.

EXAMPLE 23

4-Acetamido-N-(4-bromo-3-methyl-5-isoxazolyl)bensenesulfonamide

4-Acetamido-N-(4-bromo-3-methyl-5-isoxazolyl)bensenesulfonamide was prepared from 5-amino-4-bromo-3-methylisoxazole and 4-acetylsulfinilyl chloride according to the procedures described in Example 5. The crude product was purified by recrystallization from ethyl acetate/hexanes to give a crystalline solid, m.p. 208°–210° C., yield 56%.

EXAMPLE 24

4-Nitro-N-(4-bromo-3-methyl-5-isoxazolyl)bensenesulfonamide

4-Nitro-N-(4-bromo-3-methyl-5-isoxazolyl)bensenesulfonamide was prepared from 5-amino-4-bromo-3-methylisoxazole and 4-nitrobenzenesulfonyl chloride according to the procedures described in Example 5. The crude product was purified by recrystallization from ethyl acetate/hexanes to give a crystalline solid, m.p. 146°–149° C., yield 34%.

EXAMPLE 25

4-Butoxy-N-(4-bromo-3-methyl-5-isoxazolyl)bensenesulfonamide

4-Butoxy-N-(4-bromo-3-methyl-5-isoxazolyl)bensenesulfonamide was prepared from 5-amino-4-bromo-3-methylisoxazole and 4-butoxybenzenesulfonyl chloride according to the procedures described in Example 5. The crude product was purified by recrystallization from ethyl acetate/hexanes to give a crystalline solid, m.p. 98°–100° C., yield 33%.

EXAMPLE 26

N-(4-Bromo-3-methyl-5-isoxazolyl) benzo-2,1,3-thiadiazole-4-sulfonamide

N-(4-Bromo-3-methyl-5-isoxazolyl)benzo-2,1,3-thiadiazole-4-sulfonamide was prepared from 5-amino-4-bromo-3-methylisoxazole and 2,1,3-thiadiazole-4-sulfonyl chloride according to the procedures described in Example 5. The crude product was purified by recrystallization from ethyl acetate/hexanes to give a crystalline solid, m.p. 177°–179° C., yield 34 %.

EXAMPLE 27

N-(4-Bromo-3-methyl-5-isoxazolyl)-2-thiophenesulfonamide

N-(4-Bromo-3-methyl-5-isoxazolyl)-2-thiophenesulfonamide was prepared from 5-amino-4-bromo-3-methylisoxazole and 2-thiophenesulfonyl chloride according to the procedures described in Example 5. The crude product was purified by recrystallization from ethyl acetate/hexanes to give a crystalline solid, m.p. 125°–127° C., yield 34%.

EXAMPLE 28

3-Chloro-2-methyl-N-(4-Bromo-3-methyl-5-isoxazolyl)benzenesulfonamide

3-Chloro-2-methyl-N-(4-Bromo-3-methyl-5-isoxazolyl)benzenesulfonamide was prepared from 5-amino-4-bromo-3-methylisoxazole and 3-chloro-2-methylbenzenesulfonyl chloride according to the procedures described in Example 5. The crude product was purified by recrystallization from ethyl acetate/hexanes to give a crystalline solid, m.p. 185°–187° C., yield 34 %.

EXAMPLE 29

2,4,6-Trimethyl-N-(4-bromo-3-methyl-5-isoxazolyl)benzenesulfonamide 2,4,6-Trimethyl-N-(4-bromo-3-methyl-5-isoxazolyl)benzenesulfonamide was prepared from 5-amino-4-bromo-3-methylisoxazole and 2,4,6-trimethylbenzenesulfonyl chloride according to the procedures described in Example 1 b. The crude product was purified by recrystallization from ethyl acetate/hexanes to give a pink solid, m.p. 92°–95° C., yield 64%.

EXAMPLE 30

N-(4-bromo-3-methyl-5-isoxazolyl)-3-toluenesulfonamide

N-(4-bromo-3-methyl-5-isoxazolyl)-3-toluenesulfonamide was prepared from 5-amino-4-bromo-3-methylisoxazole and 3-toluenesulfonyl chloride according to the procedures described in Example 5. The crude product was purified by recrystallization from ethyl acetate/hexanes to give a crystalline solid, m.p. 138°–140° C., yield 63%.

EXAMPLE 31

3-Chloro- 2,5-dimethyl-N-(4-bromo-3-methyl-5-isoxazolyl)benzenesulfonamide

3-Chloro-2,5-dimethyl-N-(4-bromo-3-methyl-5-isoxazolyl)benzenesulfonamide was prepared from 5-amino-4-bromo-3-methylisoxazole and 3-chloro-2,5-dimethylbenzenesulfonyl chloride according to the procedures described in Example 5. The crude product was purified by recrystallization from ethyl acetate/hexanes to give a crystalline solid, m.p. 148°–150° C., yield 71%.

EXAMPLE 32

2,5-Difluoro-N-(4-bromo-3-methyl-5-isoxazolyl)benzenesulfonamide 2,5-Difluoro-N-(4-bromo-3-methyl-5-isoxazolyl)benzenesulfonamide was prepared from 5-amino-4-bromo-3-methylisoxazole and 4-chlorobenzenesulfonyl chloride according to the procedures described in Example 5. The crude product was purified by recrystallization from ethyl acetate/ hexanes to give a crystalline solid, m.p. 123°–125° C., yield 62%.

EXAMPLE 33

2,3,4-Trichloro-N-(4-bromo-3-methyl-5-isoxazolyl)benzenesulfonamide 2,3,4-Trichloro-N-(4-bromo-3-methyl-5-isoxazolyl)benzenesulfonamide was prepared from 5-amino-4-bromo-3-methylisoxazole and 2,3,4-trichlorobenzenesulfonyl chloride according to the procedures described in Example 5. The crude product was purified by recrystallization from ethyl acetate/hexanes to give a crystalline solid, m.p.110°–113° C., yield 66%.

EXAMPLE 34

2,3-Dichloro-N-(4-bromo-3-methyl-5-isoxazolyl)benzenesulfonamide 2,3-Dichloro-N-(4-bromo-3-methyl-5-isoxazolyl)benzenesulfonamide was prepared from 5-amino-4-bromo-3-methylisoxazole and 2,3-dichlorobenzenesulfonyl chloride according to the procedures described in Example 5. The crude product was purified by recrystallization from ethyl acetate/hexanes to give a crystalline solid, m.p. 166°–169° C., yield 75%.

EXAMPLE 35

2,5-Dichloro-N-(4-bromo-3-methyl-5-isoxazolyl)benzenesulfonamide 2,5-Dichloro-N-(4-bromo-3-methyl-5-isoxazolyl)benzenesulfonamide was prepared from 5-amino-4-bromo-3-methylisoxazole and 2,5-dichlorobenzenesulfonyl chloride according to the procedures described in Example 1 b. The crude product was purified by recrystallization from ethyl acetate/hexanes to give a yellow powder, m.p. 148°–150° C., yield 53%.

EXAMPLE 36

5-Bromo-2-methoxy-N-(4-bromo-3-methyl-5-isoxazolyl)benzenesulfonamide

5-Bromo-2-methoxy-N-(4-bromo-3-methyl-5-isoxazolyl)benzenesulfonamide was prepared from 5-amino-4-bromo-3-methylisoxazole and 5-bromo-2-methoxybenzenesulfonyl chloride according to the procedures described in Example 5. The crude product was purified by recrystallization from ethyl acetate/hexanes to give a crystalline solid, m.p. 92°–195° C., yield 61%.

EXAMPLE 37

2-Bromo-N-(4-bromo-3-methyl-5-isoxazolyl)benzenesulfonamide

2-Bromo-N-(4-bromo-3-methyl-5-isoxazolyl)benzenesulfonamide was prepared from 5-amino-4-bromo-3-methylisoxazole and 2-bromobenzenesulfonyl chloride according to the procedures described in Example 5. The crude product was purified by recrystallization from ethyl acetate/hexanes to give a crystalline solid, m.p. 84°–86° C., yield 31%.

EXAMPLE 38

2-Cyano-N-(4-bromo-3-methyl-5-isoxazolyl)benzenesulfonamide

2-Cyano-N-(4-bromo-3-methyl-5-isoxazolyl)benzenesulfonamide was prepared from 5-amino-4-bromo-3-methylisoxazole and 4-chlorobenzenesulfonyl chloride according to the procedures described in Example 5. The crude product was purified by recrystallization from ethyl acetate/hexanes to give a crystalline solid, m.p. 152°–155° C., yield 70%.

EXAMPLE 39

2,4,5-Trichloro-N-(4-bromo-3-methyl-5-isoxazolyl)bensenesulfonamide 2,4,5-Trichloro-N-(4-bromo-3-methyl-5-isoxazolyl)benzenesulfonamide was prepared from 5-amino-4-bromo-3-methylisoxazole and 2,4,5-trichlorobenzenesulfonyl chloride according to the procedures described in Example 5. The crude product was purified by recrystallization from ethyl acetate/hexanes to give a crystalline solid, m.p. 179°–182° C., yield 67%.

EXAMPLE 40

3,4-Dichloro-N-(4-bromo-3-methyl-5-isoxazolyl)benzenesulfonamide 3,4-Dichloro-N-(4-bromo-3-methyl-5-isoxazolyl)benzenesulfonamide was prepared from 5-amino-4-bromo-3-methylisoxazole and 3,4dichlorobenzenesulfonyl chloride according to the procedures described in Example 5. The crude product was purified by recrystallization from ethyl acetate/hexanes to give a crystalline solid, m.p. 144°–146° C., yield 60%.

EXAMPLE 41

3,4-Dimethoxy-N-(4-bromo-3-methyl-5-isoxazolyl)benzenesulfonamide 3,4-Dimethoxy-N-(4-bromo-3-methyl-5-isoxazolyl)benzenesulfonamide was prepared from 5-amino-4-bromo-3-methylisoxazole and 3,4-dimethoxybenzenesulfonyl chloride according to the procedures described in Example 5. The crude product was purified by recrystallization from ethyl acetate/hexanes to give a crystalline solid, m.p. 136°–138° C., yield 64 %.

EXAMPLE 42

2,4-Dichloro-N-(4-bromo-3-methyl-5-isoxazolyl)benzenesulfonamide 2,4-Dichloro-N-(4-bromo-3-methyl-5-isoxazolyl)benzenesulfonamide was prepared from 5-amino-4-bromo-3-methylisoxazole and 2,4-dichlorobenzenesulfonyl chloride according to the procedures described in Example 5. The crude product was purified by recrystallization from ethyl acetate/hexanes to give a crystalline solid, m.p. 138°–141° C., yield 46%.

EXAMPLE 43

N-(4-Iodo-5-methyl-3-isoxazolyl)benzenesulfonamide (a) 3-amino-4-Iodo-5-methylisoxazole 3-Amino-4-iodo-5-methylisoxazole was prepared from 3-amino-5-methylisoxazole and N-iodosuccinimide as described in Example 10a in 46% yield, m.p. 115°–117° C.

(b)
N-(4-Iodo-5-methyl-3-isoxazolyl)benzenesulfonamide

N-(4-Iodo-5-methyl-3-isoxazolyl)benzenesulfonamide was prepared from 3-amino-4-iodo-5-methylisoxazole and benzenesulfonyl chloride according to the procedures described in Example 2b. The crude product was purified by recrystalization from ethyl acetate/hexanes to give a brown powder m.p. 138°–141° C., yield 46%.

EXAMPLE 44

4-Nitro-N-(4-bromo-5-methyl-3-isoxazolyl)benzenesulfonamide

4-Nitro-N-(4-bromo-5-methyl-3-isoxazolyl)benzenesulfonamide was prepared from 5-amino-4-bromo-3-methylisoxazole and 4-nitrobenzene-sulfonyl chloride according to the procedures described in Example 1 b. The crude product was purified by recrystallization from ethyl acetate/hexanes to give a light tan solid, m.p. 161°–163° C., yield 55%.

EXAMPLE 45

3-Nitro-N-(4-bromo-5-methyl-3-isoxazolyl)benzenesulfonamide

3-Nitro-N-(4-bromo-5-methyl-3-isoxazolyl)benzenesulfonamide was prepared from 5-amino-4-bromo-3-methylisoxazole and 3-nitrobenzenesulfonyl chloride according to the procedures described in Example 1 b. The crude product was purified by recrystallization from ethyl acetate/hexanes, resulting in an off white powder, m.p. 137°–139° C., yield 72 %.

EXAMPLE 46

4-Trifluoromethyl-N-(4-bromo-3-methyl-5-isoxazolyl)benzenesulfonamide

4-Trifluoromethyl-N-(4-bromo-3-methyl-5-isoxazolyl)benzenesulfonamide was prepared from 5-amino-4-bromo-3-methylisoxazole and 4-trifluoromethylbenzenesulfonyl chloride according to the procedures described in Example 5. The crude product was purified by recrystallization from ethyl acetate/hexanes to give a crystalline solid, m.p. 155°–158° C., yield 72%.

EXAMPLE 47

3-Trifluoromethyl-N-(4-bromo-3-methyl-5-isoxazolyl)benzenesulfonamide

3-Trifluoromethyl-N-(4-bromo-3-methyl-5-isoxazolyl)benzenesulfonamide was prepared from 5-amino-4-bromo-3-methylisoxazole and 3trifluoromethylbenzenesulfonyl chloride according to the procedures described in Example 5. The crude product was purified by recrystallization from ethyl acetate/hexanes to give a crystalline solid, m.p. 113°–115° C., yield 83%.

EXAMPLE 48

2,5-Dimethoxy-N-(4-bromo-3-methyl-5-isoxazolyl)benzenesulfonamide 2,5-Dimethoxy-N-(4-bromo-3-methyl-5-isoxazolyl)benzenesulfonamide was prepared from 5-amino-4-bromo-3-methylisoxazole and 2,5-dimethoxybenzenesulfonyl chloride according to the procedures described in Example 5. The crude product was purified by recrystallization from ethyl acetate/hexanes to give a crystalline solid, m.p. 118°–120° C. yield 58%.

EXAMPLE 49

5-Chloro-2-methoxy-N-(4-bromo-3-methyl-5-isoxazolyl)benzenesulfonamide

5-Chloro-2-methoxy-N-(4-bromo-3-methyl-5-isoxazolyl)benzenesulfonamide was prepared from 5-amino-4-bromo-3-methylisoxazole and 5-chloro-2-methoxybenzenesulfonyl chloride according to the procedures described in Example 5. The crude product was purified by recrystallization from ethyl acetate/hexanes to give a crystalline solid, m.p. 180°–184° C., yield 61%.

EXAMPLE 50

3-Chloro-N-(4-bromo-3-methyl-5-isoxazolyl)benzenesulfonamide

3-Chloro-N-(4-bromo-3-methyl- 5-isoxazolyl)benzenesulfonamide was prepared from 5-amino-4-bromo-3-methylisoxazole and 4-trifluoromethylbenzenesulfonyl chloride according to the procedures described in Example 5. The crude product was purified by recrystallization from ethyl acetate/hexanes to give a crystalline solid, m.p. 132°–134° C., yield 68%.

EXAMPLE 51

5-Dimethylamino-N-(4-bromo-3-methyl-5-isoxazolyl)-1-naphthalenesulfonamide

5-Dimethylamino-N-(4-bromo-3-methyl-5-isoxazolyl)-1-naphthalenesulfonamide was prepared from 5-amino-4-bromo-3-methylisoxazole and 5-dimethylaminonaphthalenesulfonyl chloride according to the procedures described in Example 5. The crude product was purified by recrystallization from ethyl acetate/hexanes to give a crystalline solid, m.p. 87°–89° C., yield 68%.

EXAMPLE 52

5-Dimethylamino-N-(4-bromo-5-methyl-3-isoxazolyl)-1-naphthalenesulfonamide

5-Dimethylamino-N-(4-bromo-5-methyl-3-isoxazolyl)-1-naphthalenesulfonamide was prepared using the method of Example 2b, except that the reaction was carried out at room temperature.

EXAMPLE 53

N-(4-Bromo-3-trifluoromethyl-5-isoxazolyl)benzenesulfonamide

(a) 5-Amino-4-methoxycarbonyl-3-trifluoromethylisoxazole

Triethylamine (20 ml, 142 mmol) was added dropwise to a cold (0° C.) solution of methyl cyanoacetate (5.62 g, 56.7 mmol) and trifluoroacetic anhydride (14.3 g, 68 mmol) in dichloromethane (100 ml). The reaction was warmed to room temperature for over an hour and was stirred at room temperature for an additional hour. The reaction mixture was diluted with dichloromethane (50 ml) and washed with 1N hydrochloric acid (100 ml). The dried organic layer was placed in a 500 ml round bottom flask and oxalyl chloride (24.7 ml, 284 mmol) was then added slowly at room temperature. When gas evolution subsided, pyridine (1 ml) was added and the mixture was heated under reflux for 4 h. The reaction mixture was cooled and poured into water. The organic layer was washed with saturated sodium carbonate solution, dried over anhydrous magnesium sulfate, filtered and the solvent evaporated to give 7.14 g brown oil. Hydroxylamine hydrochloride (3.17 g, 45.6 mmol) and water (100 ml) were added to the brown oil. Sodium hydroxide solution (10%) was then slowly added to adjust the pH to about 9. After 20 min, the precipitate was filtered off and recrystallized from methanol/water to afford 6.8 g (84% yield) 5-amino-4-methoxy-carbonyl-3-trifluoromethyslisoxazole as a yellowish solid.

(b) N-(4-Methoxycarbonyl-3-trifluoromethyl-5-isoxazolyl)-benzenesulfonamide N-(4-Methoxycarbonyl-3-trifluoromethyl-5-isoxazolyl)benzenesulfonamide was prepared as described in Example 25 from 5-amino-4-methoxycarbonyl-3-trifluoromethylisoxazole and benzenesulfonyl chloride in 85% yield. The crude product was purified by recrystallization from methanol/water to give a solid, m.p. 100°–101° C.

(c) N-(4-Carboxyl-3-trifluoromethyl-5-isoxazolyl)benzenesulfonamide

N-(4-Methoxycarbonyl-3-trifluoromethyl-5-isoxazolyl)benzenesulfonamide (200 mg, 0.57 mmol) was dissolved in 1N sodium hydroxide (100 ml) stirred at room temperature for 2 h. The reaction mixture was cooled, acidified to pH 1 with concentrated hydrochloric acid and extracted with chloroform. The extract was dried over anhydrous magnesium sulfate and concentrated to give a white solid (191 mg, 100% yield)that, with decarboxylation, melts between 175°–190° C.

(d) N-(3-Trifluoromethyl-5-isoxazolyl)benzenesulfonamide

N-( 4-Carboxyl- 3-trifluoromethyl-5-isoxazolyl)benzenesulfonamide (100 mg, 0.30 mmol) was heated under reflux in N,N-dimethylformamide for 7 h. The reaction was cooled and the solvent was evaporated in vacuo. The residue was recystallized from methanol/water to give 69 mg (80% yield) off-white needles, m.p. 101°–102° C.

(e) N-(4-Bromo-3-trifluoromethyl-5-isoxazolyl)benzenesulfonamide

N-Bromosuccinimide (64 mg, 0.35 mmol) and triethylamine (0.072 ml, 0.51 mmol) were added to a solution of N-(3-trifluoromethyl-5isoxazolyl)benzenesulfonamide( 100 mg, 0.34 mmol)in chloroform (20 ml) at room temperature. The reaction was stirred at room temperature for 2 h. Chloroform (30 ml) was added and the solution was washed with 1N hydrochloric acid (40 ml), dried over magnesium sulfate and concentrated. The crude product was purified by HPLC to afford 114 mg (90%) N-(4-bromo-3-trifluoromethyl-5-isoxazolyl)benzenesulfonamide as an off-white solid, m.p. 104°–105° C.

EXAMPLE 54

2,5-diethyl-N-(3,4-dimethyl-5-isoxazolyl)benzenesulfonamide and 2,5-diethyl-N-(4-bromo-3-methyl-5-isoxazolyl)benzenesulfonamide These compounds were prepared from 5-amino-3,4-dimethylisoxazole and 2,5-diethyl-N-(3,4-dimethyl-5-isoxazoyl)benzenesulfonamide or 2,5-diethyl-N-(4-bromo-3-methyl-5-isoxazoyl)benzenesulfonamide. 2,5-Diethyl-N-(3,4-dimethyl-5-isoxazoyl)benzenesulfonamide or 2,5-diethyl-N-(4-bromo-3-methyl-5-isoxazoyl)benzenesulfonamide were added to a solution of 5-amino-3,4-dimethylisoxazole (200 mg, 1.78 mmol)in dry pyridine (2.0 ml) and the resulting mixture was stirred at room temperature for 4 h. Pyridine was removed under reduced pressure and the residue was partitioned between water and ethyl acetate. The organic layer was washed with 1N HCl (2×25 ml), brine (25 ml) and dried over anhydrous magnesium sulfate. Evaporation of the solvents left an oily residue that, after purification by column chromatography over silica gel (1% methanol in chloroform as eluent), yielded 320 mg (58%) of an off white solid. Further purification was achieved by recrystallization.

EXAMPLE 55

Assays for identifying compounds that exhibit endothelin antagonistic and/or agonist activity Compounds that are potential endothelin antagonists are identified by testing their ability to compete with $^{125}$I-labeled ET-1 for binding to human $ET_A$ receptors or $ET_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for $ET_B$ receptors can be assess by testing the ability of the compounds are to inhibit endothelin-1 induced prostacyclin release from cultured bovine aortic endothelial cells.

A. Endothelin binding inhibition—Binding Test #1:Inhibition of binding to $ET_A$ receptors TE 671 cells (ATCC Accession No. HTB 139) express $ET_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5 mM $MgCl_2$, 0.5% Bacitracin) to a concentration of 8 µg/50 µl. $^{125}$I-endothelin-1 (3,000 cpm, 50 mL) was added to 50 µL of either: (A)endothelin-1 (for non specific binding) to give a final concentration 80 nM); (B) binding buffer (for total binding); or (C) a test compound (final concentration 1 nM to 100 µM). The membrane suspension (50 µL), containing up to 8 µg of membrane protein, was added to each of (A), (B), or (C). Mixtures were shaken, and incubated at 4° C. for 16–18 hours, and then centrifuged at 4° C. for 25 min at 2,500×g. The supernatant, containing unbound radioactivity, was decanted and the pellet counted on a Genesys multiwell gamma counter. The degree of inhibition of binding (D) was calculated according to the following equation:

$$\% D = 100 - \frac{(C) - (A)}{(B) - (A)} \times 100$$

Each test was generally performed in triplicate.

B. Endothelin binding inhibition—Binding Test #2: Inhibition of binding to $ET_B$ receptors COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/50 µl.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 min. at 190×g. The cells were resuspended in phosphate buffered saline (PBS) containing 10 mM EDTA using a Tenbroeck homogenizer. The suspension was centrifuged at 40° Ct 57,800×g for 15 min, the pellet was resuspended in 5 ml of buffer A (5mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/ml) to give a final protein concentration of 2 mg/ml.

The binding assay was performed as described above using the membrane preparation diluted to give 1 µg/50 µl of binding buffer.

C. Test for activity against endothelin-induced contraction of isolated rat thoracic aortic rings The effectiveness of the test compound as an antagonist or agohist of the biological tissue response of endothelin also is assessed by measuring the effect on endothelin induced contraction of isolated rat thoracic aortic rings (see, e.g., Borges et al. (1989) *Eur. J. Pharmacol.* 165:223–230) or by measuring the ability to contract the tissue when added alone.

Compounds to be tested are prepared as 100 µM stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'- Henseleit solution saturated with a gas mixture of 95% $O_2$ and 5% $CO_2$ (118 mM NaCl, 4,7 mM KCl; 1.2 mM $MgSO_4$, 1.2 mM $KH_2PO_4$, 25 mM $NaHCO_3$, 2.5 mM $CaCl_2$, 10 mM D-glucose)gassed with 95% $O_2$/5% $CO_2$. Changes in tension are measured isometrically and recorded using a Grass Polygraph coupled to a force transducer.

Endothelin is added to the organ bath in a cumulatively increasing manner, and the effects of the test compounds on the concentration-response curve for endothelin-1 are examined. Compounds are added 15 min prior to the addition of endothelin-1.

D. Assay for identifying compounds that have agonist and/or antagonistic activity against $ET_B$ receptors

1. Stimulation of prostacyclin release

Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and subcultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d)test compound+endothelin-1 (10 nM).

After a 15 rain incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-1 6-keto $PGF_{1\alpha}$ release possess antagonist activity.

2. Inhibition of sarafotoxin 6 c induced contraction

Sarafotoxin 6 c is a specific $ET_B$ antagonist that contracts rat fundal stomach strips. The effectiveness of tests compounds to inhibit this sarafotoxin 6 c-induced contraction of rat fundal stomach strips is used as a measure $ET_B$ antagonist activity. Two isolated rat fundal stomach strips are suspended under a 1 g load in a 10 ml organ bath filled with Krebs'-Henseleit solution containing 10 µM cyclo(D-Asp-Pro-D-Val-Leu-D-Trp) (BQ-123; see, Ishikawa et al. U.S. Pat. No. 5,114,918), 5 µM indomethacin, and saturated with a gas mixture of 95% $O_2$/5% $CO_2$. Changes in tension are measured isometrically and recorded using a Grass Polygraph coupled to a force transducer. Sarafotoxin 6 c is added cumulatively to one strip while the second strip is preincubated for 15 min. with a test compound prior to addition of cumulative doses of sarafotoxin 6 c. The effects of the test compounds on the concentration-response curve for sarafotoxin 6 c are examined.

E. Results

The $IC_{50}$ for each of the compounds of the preceding Examples for $ET_A$ and $ET_B$ receptors has been measured. Almost all of the compounds have an $IC_{50}$ of less than 10 µM for either or both of the $ET_A$ and $ET_B$ receptors. Many of the compounds have an $IC_{50}$ less than about 10 µM, others have an $IC_{50}$ less than about 1 µM and some of the compounds have an $IC_{50}$ less than about 0.1 µM. A number of the compounds have an $IC_{50}$ for $ET_A$ receptors that is substantially less (10 to 100-fold or more) than for $ET_B$ receptors, and, thus are selective for $ET_A$ receptors. Others of the compounds are $ET_B$ selective.

Since modifications will be apparent to those of skill in this art, it is intended that this invention be limited only by the scope of the appended claims.

We claim:

1. A compound of formula I:

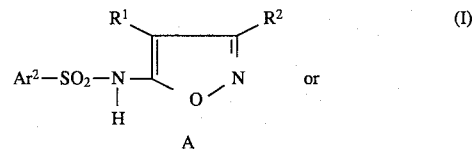

-continued

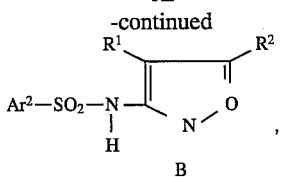

or a pharmaceutically acceptable salt of a compound of formula I, wherein:

$R^1$ is halide;

$R^2$ is selected from the group consisting of H, $NH_2$, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, hydroxyl, formyl, substituted or unsubstituted amido, and substituted or unsubstituted ureido, in which the alkyl, alkenyl and alkynyl portions contain from 1 up to about 14 carbon atoms and are either straight or branched chains or cyclic, and the aryl portions contain from about 3 to about 16 carbons; and $Ar^2$ is selected from the group consisting of:

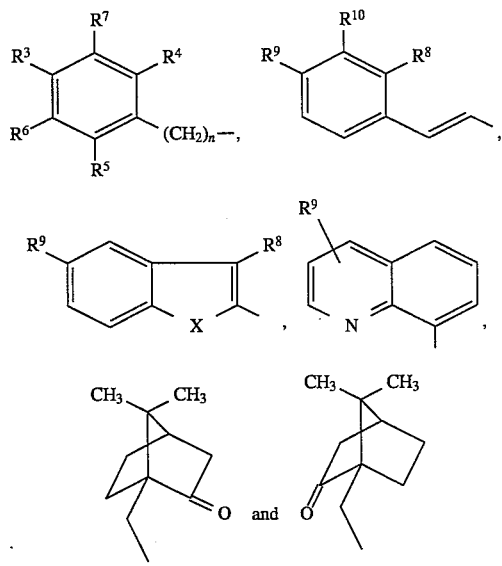

in which $R^3, R^4, R^5, R^6, R^7, R^8, R^9, R^{10}$ and $R^{11}$ are either (i), (ii), (iii) or (iv): HERE (i) $R^4, R^5, R^6$, and $R^7$ are each selected independently from the group consisting of H, NHOH, $NH_2$, $NO_2$, $N_3$, aminoalkyl, alkylamino, dialkylamino, dialkylaminoalkyl, carboxyl, carbonyl, hydroxyl, halide, pseudohalide, alkyl, alkenyl, alkynyl, aryl, heteroaryl, alkoxy, alkylamino, alkylthio, alkyalkoxy, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido, substituted or unsubstituted ureido in which the alkyl, alkenyl, alkynyl portions are straight or branched chains of from 1 up to 10 carbons and the aryl portions contain from 3 to 10 carbons, and $R^3$ is selected from the group consisting of H, carboxyl, carbonyl, hydroxyl, halide, pseudohalide, alkyl, alkenyl, alkynyl, aryl, heteroaryl, alkoxy, alkylamino, alkylthio, alkyalkoxy, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido, substituted or unsubstituted ureido in which the alkyl, alkenyl, alkynyl portions are straight or branched chains of from 1 up to 10 carbons and the aryl portions contain from 3 to 10 carbons;

$R^8, R^9$ and $R^{10}$ are each independently selected from H, $NH_2$, $NO_2$ and halide; X is O, S or $NR^{11}$ in which $R^{11}$ is H, alkyl, alkylcarbonyl or formyl; and n is from 0 up to about 6; or, alternatively, (ii) $R^4$ and $R^7$ together are substituted or unsubstituted 1,3-butadienyl, 4-dimethylamino-1,3 butadiene, 1-chloro-1,3-butadiene, 4-diemthylamino-1,3-butadienyl, 1-aza-1,3-butadienyl or 2-aza-1,3-butadienyl groups; and n, X, $R^3, R^5, R^6, R^8, R^9, R^{10}$ and $R^{11}$ are as defined in (i) above; or alternatively, (iii) $R^7$ and $R^3$ together are substituted or unsubstituted 1,3-butadienyl, 4-dimethylamino-1,3 butadiene, 1-chloro-1,3-butadiene, 4-diemthylamino-1,3-butadienyl, 1-aza-1,3-butadienyl or 2-aza-1,3-butadienyl groups; and n, X, $R^4, R^5, R^6, R^8, R^9, R^{10}$ and $R^{11}$ are as defined in (i); or alternatively (iv) $R^3, R^5$, and $R^7$ are H; and $R^4$ and $R^6$ are each independently selected from the group consisting of alkyl, alkoxy, halide, amino alkyl and dialkylaminoalkyl in which the alkyl and alkoxy groups contain from 1 to 10 carbons, and are straight or branched chains; and $R^8, R^9, R^{10}$ and $R^{11}$ are as defined in (i).

2. The compounds of claim 1, wherein all of the alkyl substituents are lower alkyl, containing from 1 to 6 carbons; the aryl substituents, other than $Ar^2$, contain from 3 to 6 carbons; and $Ar^2$ is as defined in claim 1.

3. The compounds of claim 1, wherein $Ar^2$ is selected from the group consisting of

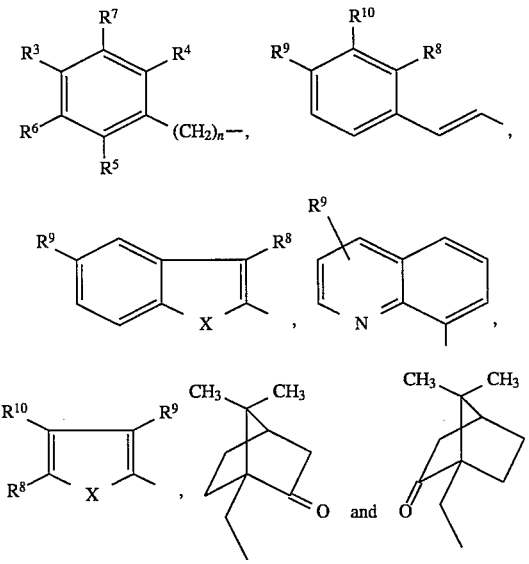

4. The compounds of claim 1, where $R^2$ is selected from the group consisting of alkyl, lower alkenyl, lower alkynyl, lower haloalkyl, halide, pseudohalide or H.

5. The compounds of claim 1, wherein $R^1$ is Br or Cl; and n is 0 or 1.

6. The compounds of claim 4, wherein $R^1$ is Br or Cl; n is 0 or 1; and $R^3, R^4, R^5, R^6, R^7, R^8, R^9, R^{10}$ and $R^{11}$ are either (i), (ii), (iii), or (iv):

(i) $R^4$ and $R^7$ are each independently selected from the group consisting of H, lower alkyl, $NH_2$, $NO_2$, halide, pseudohalide; and $R^3$ is selected from the group consisting of H, NHOH, $NH_2$, $NO_2$, $N_3$, halide, pseudohalide, alkyl, alkenyl, alkynyl, aryl, heteroaryl, alkoxy, alkylamino, dialkylamino, dialkylaminoalkyl, alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted and unsubstituted amido, substituted or unsubstituted ureido, in which the alkyl, alkenyl, alkynyl portions are straight or branched chains of from 1 up to 6 carbons and the aryl portions contain from 3 to 6 carbons; $R^5$, $R^6$, $R^{10}$ are H; $R^{11}$ is H or $CH_3$; $R^8$ and $R^9$ are each selected independently from the group consisting of H, $NO_2$, $NH_2$ and halide; or (ii) $R^4$ and $R^7$ together form 1,3-butadienyl, 4-chloro-1,3-butadienyl, 4-diemthylamino- 1,3-butadienyl, or 1-aza-1,3-butadienyl; and $R^3$, $R^5$, $R^6$, $R^8$, $R^9$, $R^{10}$ and $R^{11}$ are defined as in (i) of this embodiment; or (iii) $R^7$ and $R^3$ together form 1,3-butadienyl, 3-chloro-1,3-butadienyl, 4-diemthylamino-1,3-butadienyl, or 1-aza-1,3-butadienyl; and $R^4$, $R^5$, $R^6$, $R^8$, $R^9$, $R^{10}$ and $R^{11}$ are as defined in (i)

(iv) $R^3$, $R^5$, and $R^7$ are H; and $R^4$ and $R^6$ are each independently selected alkyl, amino alkyl and dialkylaminoalkyl in which the alkyl and alkoxy groups contain from 1 to 6 carbons, and are straight or branched chains; and $R^8$, $R^9$, $R^{10}$ and $R^{11}$ are as defined in (i).

7. The compounds of claim 1, wherein $R^2$ is selected from the group consisting of H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n—$C_3H_7$, iso—$C_3H_7$, $nC_{13}H_{27}$ and $nC_9H_{19}$; $R^1$ is Cl or Br; X is NH, O or S; n is 0 or 1: and $R^3$, $R^4$, $R^5$, $R^6$, $R^7$, $R^8$, $R^9$, $R^{10}$ and $R^{11}$ are either (i), (ii), (iii) or (iv):

(i) $R^8$ and $R^9$ are H, $NO_2$, $NH_2$ or halide; $R^5$, $R^6$ and $R^{11}$ are H; $R^4$ and $R^7$ are each independently selected from the group consisting of H, halide, $NH_2$, $CF_3$, Ph, $CH_3$; and $R^3$ is selected from the group consisting of H, NHOH, $NH_2$, $EtNH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n—$C_4H_9O$, $CH_2=CH$, Ph—$CH=CH$, $CH\equiv C$, dimethylaminomethyl, Ph—$CH\equiv C$, Ph, 3-(ethyoxycarbonylmethyl)ureido, and 3-cyclohexylureido; or (ii) $R^4$ and $R^7$ together form 1, 3-butadienyl, 4-chloro-1,3-butadienyl, 4-diamino-1,3-butadienyl or 1-aza-1,3-butadienyl; and $R^3$, $R^5$, $R^6$, $R^8$, $R^9$, $R^{10}$ and $R^{11}$ are defined as in (i); or (iii) $R^7$ and $R^3$ together form 1,3-butadienyl, 3-chloro-1,3-butadienyl, 4-diamino-1,3-butadienyl or 1-aza-1,3-butadienyl; and $R^4$, $R^5$, $R^6$, $R^8$, $R^9$, $R^{10}$ and $R^{11}$ are as defined in (i); or (iv) $R^3$, $R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8$, $R^9$, $R^{10}$ and $R^{11}$ are as defined in (i).

8. The compounds of claim 1, wherein $R^1$ is Br or Cl; $R^2$ is H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n—$C_3H_7$, iso—$C_3H_7$, $nC_{13}H_{27}$ and $nC_9H_{19}$; and $Ar^2$ is a substituted or unsubstituted phenyl group; and $R^3$, $R^4$, $R^5$, $R^6$ and $R^7$ are either (i), (ii) or (iii):

(i) $R^5$, $R^6$ and $R^7$ are H; n is 0; $R^3$ is H, $NH_2$, $CH_3$ $CF_3$, halide, $C_2H_5NH$ or Ph; $R^4$ is H, $CF_3$, $NH_2$; $R^7$ is H or $CF_3$; and $R^5$ and $R^6$ are H; or (ii) n is 1; $R^3$ is H, $NH_2$ or halide; $R^4$ is H, $CH_3$, Br, Cl, F, $CF_3$, $NH_2$, $R^7$ is H, $CH_3$, Br, Cl, F, $NH_2$ or $CF_3$; and $R^5$ and $R^6$ are H; or (iii) $R^3$, $R^5$, and $R^7$ are H; and $R^4$ and $R^6$ are each independently selected from the group consisting of alkyl groups that contain from 1 to 3 carbons.

9. The compounds of claim 1, wherein $R^1$ is Br or Cl; $R^2$ is H, $CH_3$, $C_2H_5$, $C_2F_5$ or $CF_3$; and $Ar^2$ is a substituted or unsubstituted naphthyl group or thianaphthyl group in which and $R^3$, $R^4$, $R^5$, $R^6$ and $R^7$ are either (i) or (ii):

(i) $R^3$, $R^5$ and $R^6$ are H; n is 0 and $R^4$ and $R^7$ together form 1,3-butadienyl, 4-dimethylamino-1,3 butadienyl, 1-chloro-1,3-butadiene, or 4-chloro-1,3-butadienyl; or (ii) $R^4$, $R^5$, $R^6$, $R^8$, $R^9$, $R^{10}$ and $R^{11}$ are H; n is 0; and $R^7$ and $R^3$ together form 1,3-butadienyl, 4-dimethylamino-1,3-butadiene, 1-chloro-1,3-butadiene, 1 -aza- 1,3-butadienyl.

10. The compounds of claim 8, wherein $R^1$ is Br.
11. The compounds of claim 8, wherein $R^3$, $R^5$, $R^7$ are H.
12. The compounds of claim 11, wherein $R^3$, $R^5$, and $R^7$ are H; and $R^4$ and $R^6$ are each independently selected from the group consisting of alkyl groups that contain from 1 to 3 carbons.
13. The compounds of claim 9, wherein $R^1$ is Br.
14. The compounds of claim 1, wherein $R^1$ is Br or Cl; $R^2$ is selected from the group consisting of H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n—$C_3H_7$, iso—$C_3H_7$ and $C_4H_9$; and $Ar^2$ is selected from the group consisting of substituted or unsubstituted thiophenes, furans, a pyrroles, indoles, benzofurans, quinolines, isoquinolines, styrenes and thianaphthalenes in which $R^1$ is Cl or Br; X is NH, O or S; n is 0 or 1; in (i) $R^8$ and $R^9$ are H, $NO_2$, $NH_2$ or halide; $R^5$, $R^6$ and $R^{11}$ are independently selected from the group consisting of H, $CF_3$, halide, Cl and $NH_2$; $R^4$ and $R^7$ are each independently selected from the group consisting of H, halide, $NH_2$, $CF_3$, Ph, $CH_3$; and $R^3$ is selected from the group consisting of H, NHOH, $NH_2$, $EtNH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n—$C_4H_9O$, $CH_2=CH$, Ph—$CH=CH$, $CH\equiv C$, Ph—$CH\equiv C$, Ph, 3-(ethyoxycarbonylmethyl)ureido, and 3-cyclohexylureido; and in (iv)$R^3$, $R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8$, $R^9$, $R^{10}$ and $R^{11}$ are as defined in (i).

15. The compounds of claim 14, wherein $R^1$ is Br.
16. The compounds of claim 14, wherein $R^2$ is H, $CH_3$, $C_2H_5$, or $CF_3$; in (i) $R^3$ is H, $NH_2$, $CH_3$ $CF_3$, halide or $C_2H_5NH$; $R^4$, $R^5$ and $R^6$ are H; $R^7$ is selected from the group consisting of H, $CH_3$, $CH_2C_5H_5$, $(CH_3)CH$, F or $CF_3$, and $R^8$, $R^9$ and $R^{10}$ are independently selected from the group consisting of H, $NO_2$, $NH_2$ or halide; and $R^{11}$ is H; and in (iv) $R^3$, $R^5$, and $R^7$ are H; and $R^4$ and $R^6$ are each independently selected from the group consisting of alkyl groups that contain from 1 to 3 carbons, and are straight or branched chains; and $R^8$, $R^9$, $R^{10}$ and $R^{11}$ are as defined in (i).

17. The compounds of claim 1, wherein in (i) $R^4$, $R^5$, $R^6$ and $R^7$ are each independently selected from the group consisting of H, halide, $NH_2$, $CF_3$, Ph and $CH_3$; $R^3$ is selected from H, NHOH, $NH_2$, $C_2H_5NH_2$, $(CH_3)_2NH$, Ph—$CH_2NH$, $NO_2$, F, Cl, Br, I, CN, $CH_3$, $(CH_3)_3C$, $C_5H_{11}$, $CH_3O$, n—$C_4H_9O$, $CH_2=CH$, Ph—$CH=CH$, $CH\equiv C$, Ph—CH≡C, Ph, 3-(ethyoxycarbonylmethyl)ureido, and 3-cyclohexylureido.

18. The compounds of claim 1, wherein $R^2$ is H, halide, $CH_3$, $C_2H_5$, or $CF_3$; and in (i) $R^3$ is H, $NH_2$, $CH_3$, $CF_3$, halide or $C_2H_5NH$; $R^4$, $R^5$ and $R^6$ are independently selected from the group consisting of H, $CF_3$, Br, Cl and $NH_2$; and $R^7$ is H, $CH_3$, $CH_2CH_5$, $(CH_3)CH$, F or $CF_3$ and in (iv) $R^4$ and $R^6$ are alkyl groups that contain from 1 to 3 carbons.

19. The compound of claim 1 that is N-(4-bromo-5-methyl-3-isoxazolyl)benzenesulfonamide.

20. The compound of claim 1 that is N-(4-bromo-5-methyl-3-isoxazolyl)-1-naphthalenesulfonamide.

21. The compound of claim 1 that is 2-chloro-4-fluoro-N-(5-methyl-3-isoxazoly)benzenesulfonamide.

22. The compound of claim 1 that is N-(4-iodo-5-methyl-3-isoxazolyl)benzenesulfonamide.

23. The compound of claim 1 that is N-(4-bromo-5-methyl-3-isoxazolyl)-8-quinolinesulfonamide.

24. The compound of claim 1 that is 5-nitro-N-(4-bromo-5-methyl-3-isoxazolyl)benzenesulfonamide.

25. The compound of claim 1 that is 5-dimethylamino-N-(4-bromo-3-methyl-5isoxazoyl)-1-napthalenesulfonamide.

26. The compound of claim 1 that is N-(3-methyl-4-bromo-5-isoxazolyl)benzenesulfonamide.

27. The compound of claim 1 that is N-(3-methyl-4-bromo-5-isoxazolyl)-1-naphthalenesulfonamide.

28. The compound of claim 1 that is N-(4-bromo-3-phenyl-5-isoxazolyl)benzenesulfonamide.

29. The compound of claim 1 that is N-(4-chloro-3-methyl-5-isoxazolyl)benzenesulfonamide.

30. The compound of claim 1 that is N-(4-bromo-3-methyl-5-isoxazolyl)-8-quinolinesulfonamide.

31. The compound of claim 1 that is 4-iso-propyl-N-(4-bromo-3-methyl-5-isoxazolyl)benzenesulfonamide.

32. The compound of claim 1 that is 4-bromo-N-(4-bromo-3-methyl-5-isoxazolyl)benzenesulfonamide.

33. The compound of claim 1 that is 4-fluoro-N-(4-bromo-3-methyl-5-isoxazolyl)benzenesulfonamide.

34. The compound of claim 1 that is 3-nitro-N-(4 bromo-3-methyl-5-isoxazolyl)benzenesulfonamide.

35. The compound of claim 1 that is N-(4-bromo-3-ethyl-5-isoxazolyl)-1-naphthalenesulfonamide.

36. The compound of claim 1 that is 4-iodo-N-(4-bromo-3-methyl-5-isoxazolyl)benzenesulfonamide.

37. The compound of claim 1 that is 4-chloro-N-(4-bromo-3-methyl-5-isoxazolyl)benzenesulfonamide.

38. The compound of claim 1 that is N-(4-bromo-3-ethyl-5-isoxazolyl)benzenesulfonamide.

39. The compound of claim 1 that is N-(4-bromo-3-methyl-5-isoxazolyl)-4-toluenesulfonamide.

40. The compound of claim 1 that is 2,5-dimethyl-N-(4-bromo-3-methyl-5-isoxazolyl)benzenesulfonamide.

41. The compound of claim 1 that is N-(4-bromo-3-methyl-5-isoxazolyl)-2-toluenesulfonamide.

42. The compound of claim 1 that is 2-fluoro-N-(4-bromo-3-methyl-5-isoxazolyl)benzenesulfonamide.

43. The compound of claim 1 that is 3-fluoro-N-(4-bromo-3-methyl-5-isoxazolyl)benzenesulfonamide.

44. The compound of claim 1 that is 2,5-dimethyl-N-(4-chloro-3-methyl-5-isoxazolyl)benzenesulfonamide.

45. The compound of claim 1 that is 4-acetamido-N-(4-bromo-3-methyl-5-isoxazolyl)benzenesulfonamide.

46. The compound of claim 1 that is 4-nitro-N-(4-bromo-3-methyl-5-isoxazolyl)benzenesulfonamide.

47. The compound of claim 1 that is 4-butoxy-N-(4-bromo-3-methyl-5-isoxazolyl)benzenesulfonamide.

48. The compound of claim 1 that is N-(4-bromo-3-methyl-5-isoxazolyl)benzo-2,1,3-thiadiazole-4-sulfonamide.

49. The compound of claim 1 that is 3-chloro-2-methyl-N-(4-bromo-3-methyl-5-isoxazolyl)benzenesulfonamide.

50. The compound of claim 1 that is 2,4,6-trimethyl-N-(4-bromo-3-methyl-5-isoxazolyl)benzenesulfonamide.

51. The compound of claim 1 that is N-(4-bromo-3-methyl-5-isoxazolyl)-2-thiophenesulfonamide.

52. The compound of claim 1 that is 2-methyl-N-(4-bromo-3-methyl-5-isoxazolyl)benzenesulfonamide.

53. The compound of claim 1 that is 3-chloro-2,5-dimethyl-N-(4-bromo-3-methyl-5-isoxazolyl) benzenesulfonamide.

54. The compound of claim 1 that is 2,5-difluoro-N-(4-bromo-3-methyl-5-isoxazolyl)benzenesulfonamide.

55. The compound of claim 1 that is 2,3,4-trichloro-N-(4-bromo-3-methyl-5-isoxazolyl)benzenesulfonamide.

56. The compound of claim 1 that is 2,3-dichloro-N-(4-bromo-3-methyl-5-isoxazolyl)benzenesulfonamide.

57. The compound of claim 1 that is 2,5-dichloro-N-(4-bromo-3-methyl-5-isoxazolyl)benzenesulfonamide.

58. The compound of claim 1 that is 5-bromo-2-methoxy-N-(4-bromo-3-methyl-5-isoxazolyl)benzenesulfonamide.

59. The compound of claim 1 that is 2-bromo-N-(4-bromo-3-methyl-5-isoxazolyl)benzenesulfonamide.

60. The compound of claim 1 that is 2-cyano-N-(4-bromo-3-methyl-5-isoxazolyl)benzenesulfonamide.

61. The compound of claim 1 that is 2,4,5-trichloro-N-(4-bromo-3-methyl-5-isoxazolyl)benzenesulfonamide.

62. The compound of claim 1 that is 3,4-dichloro-N-(4-bromo-3-methyl-5-isoxazolyl)benzenesulfonamide.

63. The compound of claim 1 that is 3,4-dimethoxy-N-(4-bromo-3-methyl-5-isoxazolyl)benzenesulfonamide.

64. The compound of claim 1 that is 2,4-dichloro-N-(4-bromo-3-methyl-5-isoxazolyl)benzenesulfonamide.

65. The compound of claim 1 that is 4-trifluoromethyl-N-(4-bromo-3-methyl-5-isoxazolyl)benzenesulfonamide.

66. A compound of claim 1 that is 4-butyl-N-(4-bromo-3-methyl-5-isoxazolyl)benzenesulfonamide.

67. A compound of claim 1 that is N-(4-bromo-3-trifluoromethyl-5-isoxazolyl)benzenesulfonamide.

68. A compound of claim 1 that is 3-chloro-N-(4-bromo-3-methyl-5-isoxazolyl)benzenesulfonamide.

69. A compound of claim 1 that is 5-chloro-2-methoxy-N-(4-bromo-3-methyl-5-isoxazolyl)benzenesulfonamide.

70. A compound of claim 1 that is 3-trifluoromethyl-N-(4-bromo-3-methyl-5-isoxazolyl)benzenesulfonamide.

71. A compound of claim 1 that is 2,5-dimethoxy-N-(4-bromo-3-methyl-5-isoxazolyl)benzenesulfonamide.

72. The compound of claim 1 that is 5-dimethylamino-N-(4-bromo-5-methyl-3-isoxazoyl)-1-napthalenesulfonamide.

73. A compound of claim 1 that is 2,5-diethyl-N-(4-bromo-3-methyl-5-isoxazolyl)benzenesulfonamide.

74. The compound of claim 1 that is N-(4-bromo-5-tert-butyl-3-isoxazolyl)benzenesulfonamide.

75. The compound of claim 1 that is N-(4-chloro-5-methyl-3-isoxazolyl)benzenesulfonamide.

76. The compound of claim 1 that is N-(4-bromo-3-tert-butyl-5isoxazolyl)benzenesulfonamide.

77. The compound of claim 1 that is 4-tert-butyl-N-(4-bromo-3-methyl-5-isoxazolyl)benzenesulfonamide.

78. A pharmaceutical composition, comprising a compound of claim 1 or a pharmaceutically acceptable salt of a compound of claim 1 in a pharmaceutically acceptable carrier.

79. A pharmaceutical composition, comprising a compound of claim 7 or a pharmaceutically acceptable salt of a compound of claim 7 in a pharmaceutically acceptable carrier.

80. A pharmaceutical composition, comprising a compound of claim 9 or a pharmaceutically acceptable salt of a compound of claim 9 in a pharmaceutically acceptable carrier.

81. A pharmaceutical composition, comprising a compound of claim 12 or a pharmaceutically acceptable salt of a compound of claim 12 in a pharmaceutically acceptable carrier.

82. A pharmaceutical composition formulated for single dosage administration, comprising an effective amount of one or more compounds of claim 1 or pharmaceutically acceptable salts of the compounds of claim 1, wherein the amount is effective for ameliorating the symptoms of an endothelin-mediated disease.

83. An article of manufacture, comprising packaging material and a compound of claim 1 or pharmaceutically acceptable salt of a compound of claim 1 contained within the packaging material, wherein the compound or salt thereof is effective for antagonizing the effects of endothelin, ameliorating the symptoms of an endothelin-mediated disorder, or inhibiting the binding of an endothelin peptide to an ET receptor with an $IC_{50}$ of less than about 10 μM; and the packaging material includes a label that indicates that the compound or salt thereof is used for antagonizing the effects of endothelin, inhibiting the binding of endothelin to an endothelin receptor or treating an endothelin-mediated disorder.

84. A compound of formula I:

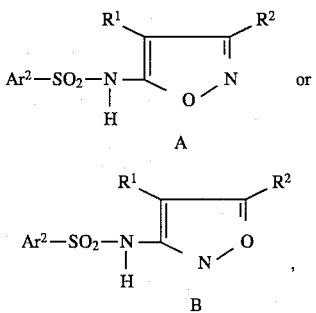

or a pharmaceutically acceptable salt of a compound of formula I, wherein:

$R^1$ is halide;

$R^2$ is selected from the group consisting of H, $NH_2$, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, hydroxyl, formyl, substituted or unsubstituted amido, and substituted or unsubstituted ureido, in which the alkyl, alkenyl and alkynyl portions contain from 1 up to about 14 carbon atoms and are either straight or branched chains or cyclic, and the aryl portions contain from about 3 to about 16 carbons; and $Ar^2$ is alkenyl, biphenyl, quinolyl, styryl, isoquinolyl, indolyl or thionaphthalyl.

85. The compounds of claim 84, where $R^2$ is selected from the group consisting of alkyl, lower alkenyl, lower alkynl, lower haloalkyl, halide, pseudohalide or H.

86. The compounds of claim 1, wherein $Ar^2$ is

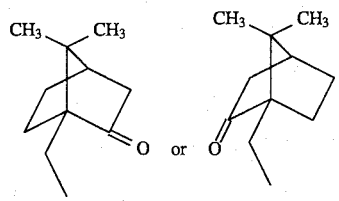

87. The compounds of claim 1, wherein $Ar^2$ is naphthyl.

88. The compounds of claim 1, wherein $Ar^2$ is quinolyl, styryl, isoquinolyl, indolyl or thionaphthalyl.

89. The compounds of claim 1 that have formula IA.

90. The compounds of claim 1 that have formula IB.

91. A compound of claim 1, wherein $R^3$ is aryl.

92. A compound of claim 2, wherein $R^3$ is aryl.

93. A compound of claim 84, wherein $Ar^2$ is biphenyl.

94. A compound of claim 93, wherein $R^2$ is hydrogen or alkyl.

* * * * *

UNITED STATES PATENT AND TRADEMARK OFFICE
CERTIFICATE OF CORRECTION

PATENT NO. : 5,514,691
DATED : May 7, 1996
INVENTOR(S) : Chan et al.

It is certified that error appears in the above-indentified patent and that said Letters Patent is hereby corrected as shown below:

Column 41, lines 1-8
in Claim 1, replace structure B with the following structure:

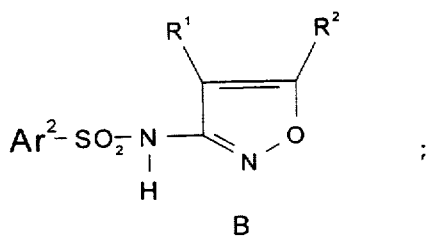

in Claim 1, column 41, line 48, replace "$R^{10\ and\ R11}$" with —$R^{10}$ and $R^{11}$—;
in Claim 1, column 41, line 55, replace "alkyalkoxy" with —alkylalkoxy—;
in Claim 1, column 41, lines 66-67, replace "alkyalkoxy" with —alkylalkoxy—;
in Claim 1, column 42, line 14, replace "1,3 butadiene" with —1,3-butadiene—;
in Claim 1, column 42, line 15, replace "diemthylamino" with —dimethylamino—;
in Claim 1, column 42, line 20, replace "1,3 butadiene" with —1,3-butadiene—;
in Claim 1, column 42, line 21, replace "diemthylamino" with —dimethylamino—;
delete Claim 3, column 42, lines 35 to 59;
in Claim 6, column 43, line 19, replace "4-diemthylamino- 1,3-butadienyl" with —4-dimethylamino-1,3-butadienyl—;
in Claim 6, column 43, line 23, replace "diemthylamino" with —dimethylamino—;
in Claim 6, column 43, line 27, insert —from— between "selected" and "alkyl";
in Claim 6, column 43, line 27, replace "amino alkyl" with —aminoalkyl—;
in Claim 7, column 43, line 35, replace "$nC_{13}H_{27}$" with —$n$-$C_{13}H_{27}$—;
in Claim 7, column 43, line 35, replace "$nC_9H_{19}$" with —$n$-$C_9H_{19}$—;
in Claim 7, column 43, line 36, replace "Oor" with —O or—;
in Claim 8, column 43, line 65, replace "$nC_{13}H_{27}$" with —$n$-$C_{13}H_{27}$—;
in Claim 8, column 43, line 65, replace "$nC_9H_{19}$" with —$n$-$C_9H_{19}$—;
in Claim 9, column 44, line 13, delete "and";

UNITED STATES PATENT AND TRADEMARK OFFICE
CERTIFICATE OF CORRECTION

PATENT NO. : 5,514,691
DATED : May 7, 1996
INVENTOR(S) : Chan et al.

It is certified that error appears in the above-indentified patent and that said Letters Patent is hereby corrected as shown below:

in Claim 9, column 44, line 15, replace "4-dimethylamino-1,3 butadiene" with —4-dimethylamino-1,3-butadiene—;

in Claim 14, column 44, line 33, between "unsubstituted" and "indoles", delete "thiophenes, furans, a pyrroles,";

in Claim 16, column 44, line 54, replace "$CH_2CH_5$" with —$CH_2CH_3$—;

in Claim 18, column 45, line 7, replace "$CH_2CH_5$" with —$CH_2CH_3$—;

delete Claim 51 in its entirety, column 46, lines 8 and 9;

in Claim 76, column 46, line 61, replace "5isoxazolyl" with —5-isoxazolyl—;

UNITED STATES PATENT AND TRADEMARK OFFICE
CERTIFICATE OF CORRECTION

PATENT NO. : 5,514,691

DATED : May 7, 1996

INVENTOR(S) : Chan et al.

Page 3 of 3

It is certified that error appears in the above-indentified patent and that said Letters Patent is hereby corrected as shown below:

in Claim 84, column 47, replace structure B with the following structure:

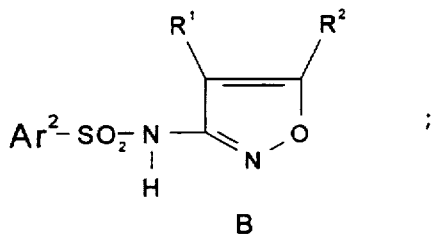

and in Claim 84, column 48, line 19, after "or", replace "thionaphthalyl" with —thianaphthyl—;

in Claim 88, column 48, line 36, after "or", replace "thionaphthalyl" with —thianaphthyl—.

Signed and Sealed this

Twenty-ninth Day of October 1996

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.    : 5,514,691 C1
DATED         : May 7, 1996
INVENTOR(S)   : Ming Fai Chan et al.

It is certified that error appears in the above-identified patent and that said Letters Patent is hereby corrected as shown below:

Column 44,
Line 15, replace "4-dimethylamino-1,3  butadiene" with -- 4-dimethylamino-1,3-butadiene --;
Line 33, between "unsubstituted" and "indoles", delete "thiophenes, furans, a pyrroles,";
Line 54, replace "$CH_2CH_5$" with -- $CH_2CH_3$ --;

Column 45,
Line 7, replace "$CH_2CH_5$" with -- $CH_2CH_3$ --;

Column 46,
Lines 8 and 9, delete Claim 51 in its entirety;
Line 61, replace "5isoxazolyl" with -- 5-isoxazolyl --;

Column 47,
Replace structure B with the following structure:

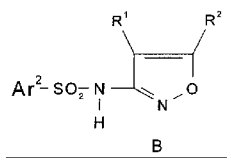

Column 48,
Lines 19 and 36, after "or", replace "thionaphthalyl" with -- thianaphthyl --.

Signed and Sealed this

Ninth Day of March, 2004

JON W. DUDAS
*Acting Director of the United States Patent and Trademark Office*

(12) REEXAMINATION CERTIFICATE (4751st)
United States Patent
Chan et al.

(10) Number: US 5,514,691 C1
(45) Certificate Issued: Mar. 18, 2003

(54) N-(4-HALO-ISOXAZOLYL)-SULFONAMIDES AND DERIVATIVES THEREOF THAT MODULATE THE ACTIVITY OF ENDOTHELIN

(75) Inventors: Ming F. Chan, San Diego, CA (US); Bore G. Raju, San Diego, CA (US); Rosario S. Castillo, San Diego, CA (US); Adam Kois, San Diego, CA (US); Chengde Wu, San Diego, CA (US); Yalamoori Venkatachalapathi, San Diego, CA (US); Erik J. Verner, San Diego, CA (US); Vitukudi N. Balaji, Encinitas, CA (US)

(73) Assignee: Texas Biotechnology Corporation, Houston, TX (US)

Reexamination Request:
No. 90/005,908, Jan. 10, 2001

Reexamination Certificate for:
Patent No.: 5,514,691
Issued: May 7, 1996
Appl. No.: 08/142,552
Filed: Oct. 21, 1993

Certificate of Correction issued May 7, 1996. 08/142,552

Related U.S. Application Data

(63) Continuation-in-part of application No. 08/100,565, filed on Jul. 30, 1993, now abandoned, and a continuation-in-part of application No. 08/100,125, filed on Jul. 30, 1993, now abandoned, and a continuation-in-part of application No. 08/065,202, filed on May 20, 1993, now abandoned.

(51) Int. Cl.$^7$ .................. A61K 31/435; C07D 261/06; C07D 215/02
(52) U.S. Cl. .................. 514/312; 514/362; 514/363; 514/378; 514/380; 546/380; 546/153; 546/155; 546/159; 546/162; 546/167; 546/172; 548/241; 548/243; 548/244; 548/245
(58) Field of Search .................. 514/312, 362, 514/363, 378, 380; 546/153, 155, 159, 162, 167, 172; 548/241, 243, 244, 245

(56) References Cited

FOREIGN PATENT DOCUMENTS

JP 63238006 10/1988

OTHER PUBLICATIONS

English language translation of JP 63–238006 (1988).

*Primary Examiner*—Joseph K. McKane

(57) ABSTRACT

N-(4-halo-isoxazolyl)sulfonamides and methods for modulating or altering the activity of the endothelin family of peptides are provided. In particular, N-(4-halo-3-isoxazolyl) sulfonamides and N-(4-halo-5-isoxazolyl) benzenesulfonamides and methods for inhibiting the binding of an endothelin peptide to an endothelin receptor or increasing the activity of endothelin peptides by contacting the receptor with a sulfonamide are provided. Methods for treating endothelin-mediated disorders by administering effective amounts of one or more of these sulfonamides or prodrugs thereof that inhibit or increase the activity of endothelin are also provided.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 84, 85, 93 and 94 is confirmed.

Claims 3, 45, 46 and 51 are cancelled.

Claims 1, 6–9, 14, 16–18 and 88 are determined to be patentable as amended.

Claims 2, 4–5, 10–13, 15, and 19–83, and 86–92, dependent on an amended claim, are determined to be patentable.

1. A compound of formula I:

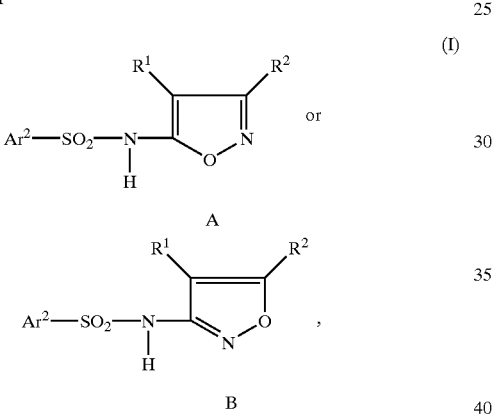

or a pharmaceutically acceptable salt of a compound of formula I, wherein:

$R^1$ is halide;

$R^2$ is selected from the group consisting of H, $NH_2$, alkyl, alkenyl, alkynyl, aryl, arylalkyl, heteroaryl, alkoxy, alkylamino, alkylthio, alkyloxy, haolalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, hydroxyl, formyl, substituted or unsubstituted amido, and substituted or unsubstituted ureido, in which the alkyl, alkenyl and alkynyl portions contain from 1 up to about 14 carbon atoms and are either straight or branched chains or cyclic, and the aryl portions contain from about 3 to about 16 carbons; and $Ar^2$ is selected from the group consisting of:

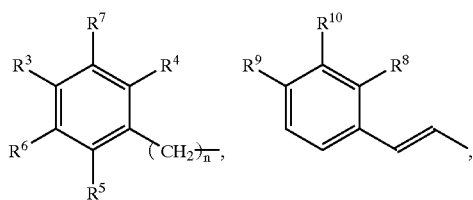

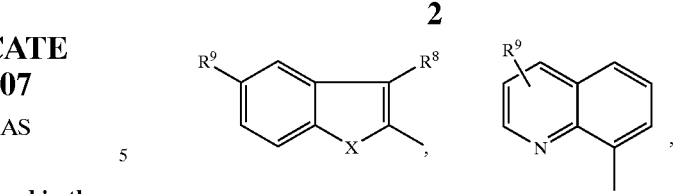

in which $R^3$, $R^4$, $R^5$, $R^6$, $R^7$, $R^8$, $R^9$, $R^{10}$ and $R^{11}$ are either (i), (ii), (iii) or (iv):

(i) $R^4$, $R^5$, $R^6$, and $R^7$ are each selected independently from the group consisting of H, NHOH, $NH_2$, $NO_2$, $N_3$, aminoalkyl, alkylamino, dialkylamino, dialkylaminoalkyl, carboxyl, carbonyl, hydroxyl, halide, pseudohalide, alkyl, alkenyl, alkynyl, aryl, heteroaryl, alkoxy, alkylamino, alkylthio, alkyalkoxy, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido, substituted or unsubstituted ureido in which the alkyl, alkenyl, alkynyl portions are straight or branched chains of from 1 up to 10 carbons and the aryl portions contain from 3 to 10 carbons, and $R^3$ is selected from the group consisting of H, carboxyl, carbonyl, hydroxyl, halide, pseudeohalide, alkyl, alkenyl, alkynyl, aryl, heteroaryl, alkoxy, alkylamino, alkylthio, alkyalkoxy, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, [substituted or unsubstituted amido,] substituted or unsubstituted ureido in which the alkyl, alkenyl, alkynyl portions are straight or branched chains of from 1 up to 10 carbons and the aryl portions contain from 3 to 10 carbons;

$R^8$, $R^9$ and $R^{10}$ are each independently selected from H, $NH_2$, $NO_2$ and halide; X is O, S or $NR^{11}$ in which $R^{11}$ is H, alkyl, alkylcarbonyl or formyl; and n is from 0 up to about 6; or, alternatively, (iii) $R^4$ and $R^7$ together are substituted or unsubstituted 1,3-butadienyl, 4-dimethylamino-1,3-butadiene, 1-chloro-1,3-butadiene, 4-dimethylamino-1,3-butadienyl, 1-aza-1,3-butadienyl or 2-aza-1,3-butadienyl groups; and n, X, $R^3$, $R^5$, $R^6$, $R^8$, $R^9$, $R^{10}$ and $R^{11}$ are as defined in (i) above; or alternatively (iii) $R^7$ and $R^3$ together are substituted or unsubstituted 1,3-butadienyl, 4-dimethylamino-1,3-butadiene, 1-chloro-1,3-butadiene, 4-dimethylamino-1,3-butadienyl, 1-aza-1,3-butadienyl or 2-aza-1,3-butadienyl groups; and n, X, $R^4$, $R^5$, $R^6$, $R^8$, $R^9$, $R^{10}$ and $R^{11}$ are as defined in (i); or alternatively (iv) $R^3$, $R^5$, and $R^7$ are H; and $R^4$ and $R^6$ are each independently selected from the group consisting of alkyl, alkoxy, halide, amino alkyl and dialkylaminoalkyl in which the alkyl and alkoxy groups contain from 1 to 10 carbons, and are straight or branched chains; and $R^8$, $R^9$, $R^{10}$ and $R^{11}$ are as defined in (i).

6. The compounds of claim 4, wherein $R^1$ is Br or Cl; n is 0 or 1; and $R^3$, $R^4$, $R^5$, $R^6$, $R^7$, $R^8$, $R^9$, $R^{10}$ and $R^{11}$ are either (i), (ii), (iii), or (iv):

(i) $R^4$ and $R^7$ are each independently selected from the group consisting of H, lower alkyl, $NH_2$, $NO_2$, halide, pseudohalide; and $R^3$ is selected from the group consisting of H, [NHOH, $NH_2$, $NO_2$, $N_3$,] halide, psuedohalide, alkyl, alkenyl, alkynyl, aryl, heteroaryl, alkoxy, alkylamino, [dialkylamino, dialkylaminoalkyl,] alkylthio, alkylalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, [substituted and unsubstituted amido,] substituted or unsubstituted ureido, in which the alkyl, alkenyl, alkynyl portions are straight or branched chains of from 1 up to 6 carbons and the aryl portions contain from 3 to 6 carbons; $R^5$, $R^6$, $R^{10}$ are H; $R^{11}$ is H or $CH_3$; $R^8$ and $R^9$ are each selected independently from the group consisting of H, $NO_2$, $NH_2$ and halide; or (ii) $R^4$ and $R^7$ together form 1,3-butadienyl, [4-chloro-1,3-butadienyl,] 4-dimethylamino-1,3-butadienyl, or 1-aza-1,3-butadienyl; and $R^3$, $R^5$, $R^6$, $R^8$, $R^9$, $R^{10}$ and $R^{11}$ are defined as in (i) of this embodiment; or (iii) $R^7$ and $R^3$ together form 1,3-butadienyl, [3-chloro-1,3-butadienyl,] 4-dimethylamino-1,3-butadienyl, or 1-aza-1,3-butadienyl; and $R^4$, $R^5$, $R^6$, $R^8$, $R^9$, $R^{10}$ and $R^{11}$ are as defined in (i);

(iv) $R^3$, $R^5$, and $R^7$ are H; and $R^4$ and $R^6$ are each independently selected from alkyl, aminoalkyl and dialkylaminoalkyl in which the alkyl and alkoxy groups contain from 1 to 6 carbons, and are straight or branched chains; and $R^8$, $R^9$, $R^{10}$ and $R^{11}$ are as defined in (i).

7. The compounds of claim 1, wherein $R^2$ is selected from the group consisting of H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n-$C_3H_7$, iso-$C_3H_7$, n-$C_{13}H_{27}$ and n-$C_9H_{19}$; $R^1$ is Cl or Br; X is NH, O or S; n is 0 or 1; and $R^3$, $R^4$, $R^5$, $R^6$, $R^7$, $R^8$, $R^9$, $R^{10}$ and $R^{11}$ are either (i), (ii), (iii) or (iv):

(i) $R^8$ and $R^9$ are H, $NH_2$, $NH_2$ or halide; $R^5$, $R^6$ and $R^{11}$ are H; $R^4$ and $R^7$ are each independently selected from the group consisting of H, halide, $NH_2$, $CF_3$, Ph, $CH_3$; and $R^3$ is selected from the group consisting of H, [NHOH, $NH_2$,] $EtNH_2$, [$(CH_3)_2NH$,] Ph—$CH_2NH$, [$NO_2$,] F, Cl, Br, I, [CN,] $CH_3$, $(CH_3)_3C$, $C_5H_{11}$, $CH_3O$, n-$C_4H_9O$, $CH_2=CH$, Ph—CH=CH, CH≡C, dimethylaminomethyl, [Ph—CH≡C] *Ph—C≡C*, Ph, 3-(ethyoxycarbonylmethyl)-ureido, and 3-cyclohexylureido; or (ii) $R^4$ and $R^7$ together form 1, 3-butadienyl, [4-chloro-1,3-butadienyl,] 4-diamino-1,3-butadienyl or 1-aza-1,3-butadienyl; and $R^3$, $R^5$, $R^6$, $R^8$, $R^9$, $R^{10}$ and $R^{11}$ are defined as in (i); or (iii) $R^7$ and $R^3$ together form 1,3-butadienyl, [3-chloro-1,3-butadienyl,] 4-diamino-1,3-butadienyl or 1-aza-1,3-butadienyl; and $R^4$, $R^5$, $R^6$, $R^8$, $R^9$, $R^{10}$ and $R^{11}$ are as defined in (i).; or (iv) $R^3$, $R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8$, $R^9$, $R^{10}$ and $R^{11}$ are as defined in (i).

8. The compounds of claim 1, wherein $R^1$ is Br or Cl; $R^2$ is H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n-$C_3H_7$, iso-$C_3H_7$, n-$C_{13}H_{27}$ and n-$C_9H_{19}$; and $Ar^2$ is a substituted or unsubstituted phenyl group; and $R^3$, $R^4$, $R^5$, $R^6$ and $R^7$ are either (i), (ii) or (iii):

(i) $R^5$, $R^6$ and $R^7$ are H; n is 0; $R^3$ is H, [$NH_2$,] $CH_3$, $CF_3$, halide, $C_2H_5NH$ or Ph; $R^4$ is H, $CF_3$, $NH_2$; $R^7$ is H or $CF_3$; and $R^5$ and $R^6$ are H; or (ii) n is 1; $R^3$ is H[, $NH_2$] or halide; $R^4$ is H, $CH_3$, Br, Cl, F, $CF_3$, $NH_2$, $R^7$ is H, $CH_3$, Br, Cl, F, $NH_2$ or $CF_3$; and $R^5$ and $R^6$ are H; or (iii) $R^3$, $R^5$, and $R^7$ are H; and $R^4$ and $R^6$ are each independently selected from the group consisting of alkyl groups that contain from 1 to 3 carbons.

9. The compounds of claim 1, wherein $R^1$ is Br or Cl; $R^2$ is H, $CH_3$, $C_2H_5$, $C_2F_5$ or $CF_3$; and $Ar^2$ is a substituted or unsubstituted naphthyl group or thianaphthyl group in which $R^3$, $R^4$, $R^5$, $R^6$ and $R^7$ are either (i) or (ii):

(i) $R^3$, $R^5$ and $R^6$ are H; n is 0 and $R^4$ and $R^7$ together form 1,3-butadienyl, 4-dimethylamino-1,3-butadiene, *or* 1-chloro-1,3-butadiene[, or 4-chloro-1,3-butadienyl]; or (ii) $R^4$, $R^5$, $R^6$, $R^8$, $R^9$, $R^{10}$ and $R^{11}$ are H; n is 0; and $R^7$ and $R^3$ together form 1,3-butadienyl, 4-dimethylamino-1,3-butadiene, 1-chloro-1,3-butadiene, 1-aza-1,3-butadienyl.

14. The compounds of claim 1, wherein $R^1$ is Br or Cl; $R^2$ is selected from the group consisting of H, $CH_3$, $C_2H_5$, $H_2C=CH$, $CH\equiv C$, Ph—O, Ph—$CH_2$, 4-$CH_3$—$C_6H_4O$, halide, $CF_3$, $C_2F_5$, n-$C_3H_7$, iso-$C_3H_7$ and $C_4H_9$; and $Ar^2$ is selected from the group consisting of substituted or unsubstituted indoles, benzofurans, quinolines, [isoquinolines,] styrenes and thianaphthalenes in which $R^1$ is Cl or Br; X is NH, O or S; n is 0 or 1; in (i) $R^8$ and $R^9$ are H, $NO_2$, $NH_2$ or halide; $R^5$, $R^6$ and $R^{11}$ are independently selected from the group consisting of H, $CF_3$, halide, Cl and $NH_2$; $R^4$ and $R^7$ are each independently selected from the group consisting of H, halide, $NH_2$, $CF_3$, Ph, $CH_3$; and $R^3$ is selected from the group consisting of H, [NHOH, $NH_2$,] $EtNH_2$, [$(CH_3)_2NH$,] Ph—$CH_2NH$, [$NO_2$,] F, Cl, Br, I, [CN,] $CH_3$, $(CH_3)_3C$, $C_5H_{11}$, $CH_3O$, n-$C_4H_9O$, $CH_2=CH$, Ph—CH=CH, CH≡C, [Ph—CH≡C] *Ph—C≡C*, Ph, 3-(ethyoxycarbonylmethyl)ureido, and 3-cyclohexylureido; and in (iv) $R^3$, $R^5$, and $R^7$ are H; and $R^4$ and $R^6$ are each independently selected from the group consisting of alkyl and aminoalkyl groups in which the alkyl groups contain from 1 to 6 carbons, and are straight or branched chains; and $R^8$, $R^9$, $R^{10}$ and $R^{11}$ are as defined in (i).

16. The compounds of claim 14, wherein $R^2$ is H, $CH_3$, $C_2H_5$, or $CF_3$; in (i) $R^3$ is H, [$NH_2$,] $CH_3$, $CF_3$, halide or $C_2H_5NH$; $R^4$, $R^5$ and $R^6$ are H; $R^7$ is selected from the group consisting of H, $CH_3$, $CH_2CH_3$, $(CH_3)CH$, F or $CF_3$, and $R^8$, $R^9$ and $R^{10}$ are independently selected from the group consisting of H, $NO_2$, $NH_2$ or halide; and $R^{11}$ is H; and in (iv) $R^3$, $R^5$, and $R^7$ are H; and $R^4$ and $R^6$ are each independently selected from the group consisting of alkyl groups that contain from 1 to 3 carbons, and are straight or branched chains; and $R^8$, $R^9$, $R^{10}$ and $R^{11}$ are as defined in (i).

17. The compounds of claim 1, wherein in (i) $R^4$, $R^5$, $R^6$ and $R^7$ are each independently selected from the group consisting of H, halide, $NH_2$, $CF_3$, Ph and $CH_3$; $R^3$ is selected from H, [NHOH, $NH_2$,] $C_2H_5NH_2$, [$(CH_3)_2NH$,] Ph—$CH_2$NH, [$NO_2$,] F, Cl, Br, I, [CN,] $CH_3$, $(CH_3)_3C$, $C_5H_{11}$, $CH_3O$, n-$C_4H_9O$, $CH_2$=CH, Ph—CH=CH, CH≡C, [Ph—CH≡C] *Ph—C≡C*, Ph, 3-(ethyoxycarbonylmethyl) ureido, and 3-cyclohexylureido.

18. The compounds of claim 1, wherein $R^2$ is H, halide, $CH_3$, $C_2H_5$, or $CF_3$; and in (i) $R^3$ is H, [$NH_2$,] $CH_3$, $CF_3$, halide or $C_2H_5NH$; $R^4$, $R^5$ and $R^6$ are independently selected from the group consisting of H, $CF_3$, Br, Cl and $NH_2$; and $R^7$ is H, $CH_3$, $CH_2CH_3$, $(CH_3)CH$, F or $CF_3$ and in (iv) $R^4$ and $R^6$ are alkyl groups that contain from 1 to 3 carbons.

88. The compounds of claim 1, wherein $Ar^2$ is quinolyl, styryl, [isoquinolyl,] indolyl or thianaphthyl.

* * * * *